(12) United States Patent
Kashi et al.

(10) Patent No.: US 9,649,383 B2
(45) Date of Patent: May 16, 2017

(54) LIQUID FORMULATIONS FOR TNFR:FC FUSION PROTEINS

(71) Applicant: MERCK SHARP & DOHME CORP., Rahway, NJ (US)

(72) Inventors: Ramesh S. Kashi, Warren, NJ (US); Shona P. Patel, Florham Park, NJ (US); Sarita Mittal, Bridgewater, NJ (US); Ashwin Basarkar, Springfield, NJ (US); Shuai Shi, Summit, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/443,557

(22) PCT Filed: Nov. 15, 2013

(86) PCT No.: PCT/US2013/070248
§ 371 (c)(1),
(2) Date: May 18, 2015

(87) PCT Pub. No.: WO2014/078627
PCT Pub. Date: May 22, 2014

(65) Prior Publication Data
US 2015/0290325 A1  Oct. 15, 2015

Related U.S. Application Data

(60) Provisional application No. 61/727,922, filed on Nov. 19, 2012.

(51) Int. Cl.
| | | |
|---|---|---|
| A61K 38/17 | (2006.01) | |
| A61K 47/26 | (2006.01) | |
| A61K 47/18 | (2006.01) | |
| A61K 47/12 | (2006.01) | |
| A61K 47/22 | (2006.01) | |
| A61K 47/02 | (2006.01) | |
| C07K 14/715 | (2006.01) | |

(52) U.S. Cl.
CPC .......... *A61K 47/26* (2013.01); *A61K 38/1793* (2013.01); *A61K 47/02* (2013.01); *A61K 47/12* (2013.01); *A61K 47/183* (2013.01); *A61K 47/22* (2013.01); *C07K 14/7151* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 6,923,956 B1 * | 8/2005 | Tschope | A61K 38/215 424/85.6 |
| 7,648,702 B2 | 1/2010 | Gombotz et al. | |
| 2010/0278822 A1 * | 11/2010 | Fraunhofer | A61K 39/39591 424/133.1 |
| 2014/0186351 A1 * | 7/2014 | Britta | A61K 47/12 424/134.1 |

FOREIGN PATENT DOCUMENTS

| | | |
|---|---|---|
| WO | 2005012353 | 2/2005 |
| WO | 2007092772 | 8/2007 |
| WO | WO2011141926 | 11/2011 |
| WO | WO2012143418 | 10/2012 |

OTHER PUBLICATIONS

McIlvaine buffer. (Sep. 16, 2015). In Wikipedia, The Free Encyclopedia. Retrieved 20:05, Jun. 16, 2016, from https://en.wikipedia.org/w/index.php?title=McIlvaine_buffer&oldid=681258150.*
Nayar et al. High throughput formulation: strategies for rapid development of stable protein products. Pharm Biotechnol. 2002;13:177-98.*

* cited by examiner

*Primary Examiner* — David Romeo

(57) ABSTRACT

The invention provides stable liquid formulations for a recombinant biopharmaceutical protein comprising a soluble form of the human p75 TNF receptor fused to an Fc domain of a human immunoglobulin protein (TNFR:Fc). Typically, biopharmaceutical proteins such as monoclonal antibodies (mAbs) and immunoglobulin fusion proteins (e.g., immunoadhesion proteins) are produced by recombinant DNA technology in mammalian cell expression systems. In order to guarantee the reproducible clinical performance of a biopharmaceutical product, manufacturers have to deliver a product of consistent and reproducible quality.

5 Claims, 13 Drawing Sheets

LIQUID FORMULATIONS FOR TNFR:FC FUSION PROTEINS

FIELD OF THE INVENTION

The present invention relates to the field of biopharmaceutical protein formulation. More specifically, the invention provides stabilized liquid formulations for a recombinant biopharmaceutical protein comprising a soluble form of the human p75 TNF receptor fused to an Fc domain of a human immunoglobulin protein (TNFR:Fc).

BACKGROUND OF THE INVENTION

Typically, biopharmaceutical proteins such as monoclonal antibodies (mAbs) and immunoglobulin fusion proteins (e.g., immunoadhesion proteins) are produced by recombinant DNA technology in mammalian cell expression systems. In order to guarantee the reproducible clinical performance of a biopharmaceutical product, manufacturers have to deliver a product of consistent and reproducible quality. It is well-established that molecular alterations can occur during every stage of the manufacturing process and those aspects of the upstream unit operations, including cell culture conditions, exposure to various buffers and solutions during the purification process and storage conditions, can each introduce heterogeneity into a mAb or Fc-fusion protein product.

Some of the molecular alterations can alter a quality attribute of a biopharmaceutical product, resulting in an undesirable change in the identity, strength or purity of the product. In addition, process-related heterogeneities can produce variant proteins characterized by alterations in either the size, chemical/charge or conformation of a biopharmaceutical protein. Furthermore, depending upon the type of host cell that is used, and the particular amino acid sequence of the protein, additional heterogeneity may also be introduced as a consequence of intracellular processes, such as post-translational modifications.

The primary goal of formulation development is to provide a pharmaceutical composition that will support the stability of a biopharmaceutical protein during all stages of its production, storage, shipping and use. The process of formulation development for an innovative biopharmaceutical protein, or a biosimilar monoclonal antibody (mAb) or a recombinant Fc-containing fusion protein (Fc-fusion protein), is essential to its safety, clinical efficacy and commercial success.

The biopharmaceutical protein etanercept (TNFR:Fc) is a Fc-fusion protein which is known to be susceptible to misfolding, fragmentation and aggregation. Therefore, there is a need for stabilizing liquid (aqueous) formulations capable of mitigating these issues when a pharmaceutical composition comprising etanercept is stored or marketed as a liquid product.

SUMMARY OF THE INVENTION

The present invention discloses stable liquid formulations comprising a soluble form of the human TNF receptor fused to an Fc domain of a human immunoglobulin protein, a citrate-phosphate or citrate buffer with a desired pH, sucrose or trehalose, sodium chloride and either L-histidine or L-asparactic acid. The disclosed formulations were developed in accordance with a defined set of selection criteria based on data collected from analytical procedures performed to evaluate the biochemical and biophysical stability of etanercept in alternative formulations.

More specifically, the present invention provides stable liquid formulations for a TNFR:Fc fusion protein, referred to herein as biosimilar etanercept, which do not comprise arginine (e.g., L-arginine). In alternative embodiments, the disclosed formulations can comprise about 25 to 50 mg/ml of etanercept.

In various embodiments, stable aqueous (liquid) formulation can be prepared having a citrate-phosphate or citrate buffer with a desired pH (e.g., within the range of pH 6.0 to pH 6.6), sucrose or trehalose, sodium chloride ($\geq 75$ mM), either L-histidine or L-aspartic acid, and an effective amount of a soluble form of the human TNFII (ie. P75) receptor fused to an Fc domain of a human immunoglobulin protein. In particular embodiments, the TNFR fusion protein is a biosimilar form of etanercept.

For example, in alternative embodiments liquid formulation comprising a soluble form of the human TNF receptor fused to an Fc domain of a human immunoglobulin protein in a 25 mM citrate-phosphate buffer (pH 6.0 or pH 6.3), further comprising about 25 mM L-histidine, sodium chloride, and about 1% sucrose or trehalose are disclosed.

In alternative embodiments, a stabilized liquid formulation comprising a soluble form of the human TNF receptor fused to an Fc domain of a human immunoglobulin protein produced in CHO cell culture, in a 25 mM citrate-phosphate buffer (pH 6.0 to pH 6.3), further comprising NaCl (>75 mM), 25 mM L-histidine, and about 1% sucrose or trehalose are disclosed.

In a particular embodiment, the invention provides a stabilized 50 mg/ml etanercept liquid formulation comprising a 25 mM citrate-phosphate buffer pH 6.3, 100 mM NaCl, 25 mM L-histidine and 1% sucrose.

In an alternative embodiment, the invention provides a stabilized 50 mg/ml etanercept liquid formulation comprising a 25 mM citrate-phosphate buffer pH 6.0, 125 mM NaCl, 25 mM L-histidine and 1% trehalose.

In yet another alternative embodiment, the invention provides a stabilized liquid formulation comprising a soluble form of the human TNF receptor fused to an Fc domain of a human immunoglobulin protein produced in CHO cell culture, in a 10 mM citrate buffer (pH 6.0 to pH 6.3), further comprising NaCl (>75 mM), 25 mM L-histidine, and about 1% sucrose or trehalose are disclosed.

In a particular embodiment, the invention provides a stabilized 50 mg/ml etanercept liquid formulation comprising a 25 mM citrate buffer pH 6.3, 100 mM NaCl, 25 mM L-aspartic acid and 1% trehalose.

DETAILED DESCRIPTION

Figure 1:
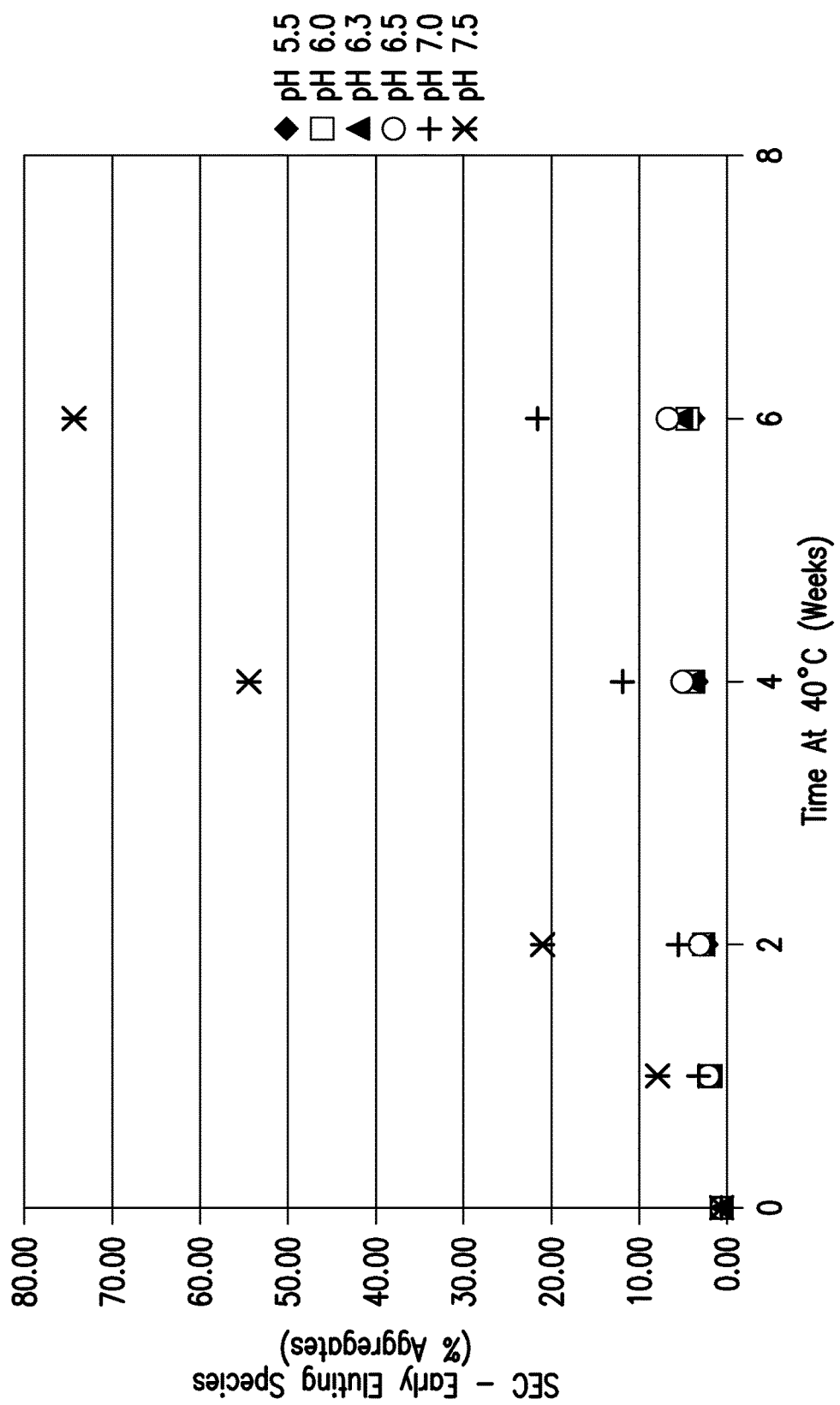
FIG. 1 provides a graphic representation of the results form a pH screening study summarizing the percentage aggregates (early eluting SEC species) versus time (in weeks) for biosimilar etanercept under accelerated conditions (40° C.).

The following definitions are provided to facilitate understanding of certain terms used throughout the specification.

As used herein, the phrase "TNFR:Fc" refers to a recombinant biopharmaceutical protein comprising a soluble form of the human p75 TNF receptor fused to an Fc domain of a human immunoglobulin protein.

As used herein the term "fusion protein" means a protein formed by fusing (i.e., joining) all or part of two polypeptides which are not the same. Typically, fusion proteins are made using recombinant DNA techniques, by end to end joining of polynucleotides encoding the two polypeptides.

As used herein the phrase "Ig fusion protein" refers to a protein which comprises a non-IgG portion linked to a portion of an IgG molecule which is derived from the constant region of a human immunoglobulin molecule.

As used herein the term "etanercept" refers to the dimeric recombinant therapeutic glycoprotein (TNFR:Fc), produced in a Chinese hamster ovary (CHO) mammalian cell expression system, and consisting of the extracellular ligand binding portion of the human 75 kilodalton (p.75, TNFRII, WO 91/03553, WO 94/06476) human tumor necrosis factor receptor linked to the constant region (Fc) of human IgG1, which comprises the active ingredient in the biopharmaceutical product ENBREL (Pfizer/Amgen). Etanercept is a dimeric fusion polypeptide consisting of the extracellular ligand-binding domain of the human 75 kilodalton (p75) tumor necrosis factor receptor (TNFR) linked to the Fc portion of human IgG1. The Fc component of etanercept contains the constant heavy 2 (CH2) domain, the constant heavy 3 (CH3) domain and the hinge region, but not the constant heavy 1 (CH1) domain of human IgG1 (U.S. Pat. No. 7,648,702 (referred to herein as the '702 patent)). It consists of 934 amino acids and has an apparent molecular weight of approximately 150 kilodaltons (US Full Prescribing Information 2006). As used herein, the term "etanercept" encompasses both biosimilar forms and the molecular forms present in the reference product. As used herein the term "ENBREL" refers to the therapeutic TNFR:Fc (etanercept) glycoprotein, produced in a Chinese hamster ovary (CHO) mammalian cell expression system, and consisting of the extracellular ligand binding portion of the human 75 kilodalton (p.75, TNFRII, WO 91/03553, WO 94/06476) human tumor necrosis factor receptor linked to the constant region (Fc) of human IgG1. Etanercept is marketed by for the treatment of at least rheumatoid arthritis, psoriatic arthritis, psoriasis and ankylosing spondylitis.

The term "pharmaceutically acceptable" is used herein in accordance with its well-known meaning in the art to denote that which is acceptable for medical or veterinary use, preferably for medical use in humans, particularly approved for use by the US Food and Drug Administration or other regulatory authority.

As used herein, the term "biosimilar" is used in a manner that is consistent with the working definition promulgated by the US FDA which defines a biosimilar product to be one that is "highly similar" to a reference product (despite minor differences in clinically inactive components). In practice there can be no clinically meaningful differences between the reference product and the biosimilar product in terms of safety, purity, and potency (Public Health Service (PHS) Act §262). The results of a double-blind, single-dose comparative pharmacokinetic (PK) crossover study conducted in 37 healthy volunteers comparing Enbrel® to the biosimilar etanercept molecule used in the formulation studies presented herein, indicate that a single subcutaneous injection of 25 mg/ml of reconstituted lyophilized biosimilar product is safe, well-tolerated. Serial blood samples were collected for 480 hours after dosing for pharmacokinetic analysis. Serum concentrations of etanercept were determined using a commercial enzyme-linked immunosorbent assay (ELISA). Comparative pharmokinetic studies demonstrated that the biosimilar etanercept molecule used herein has comparable bioavailability (based on a comparison of Cmax and AU 0-t) to Enbrel® (Yi, SoJeong et al. Biodrugs 26(3):177-184 (2012).

As used herein, the term "reference product", is used to refer to commercially available etanercept (ENBREL). ENBREL lot numbers 1026664 and 1030086 were used in the stability studies and comparisons herein for comparison purposes.

As used herein, "formulation" is a composition of a pharmaceutically active drug, such as a biologically active protein, that is suitable for parenteral administration (including but not limited to intravenous, intramuscular, or subcutaneous) to a patient in need thereof and includes only pharmaceutically acceptable excipients, diluents, and other additives deemed safe by the Federal Drug Administration or other foreign national authorities.

As used herein the phrases "liquid formulation" and "aqueous formulation" are used interchangeably to refer to a solution or liquid preparation that contains a biopharmaceutical in combination with one or more excipients (e.g., chemical additives)—dissolved in a suitable solvent.

As used herein, the phrase "pharmaceutical composition" refers to a formulation such that it is suitable for administration and/or injection into a human patient in need thereof. The term "pharmaceutical formulation" refers to preparations which are in such form as to permit the active ingredients to be effective, and which contains no additional components which are toxic to the subjects to which the formulation would be administered.

As used herein, the term "buffer" encompasses those agents which maintain the solution pH in an acceptable range. A buffer is an aqueous solution consisting of a mixture of a weak acid and its conjugate base or a weak base and its conjugate acid. Its pH changes very little when a small amount of strong acid or base is added to it and thus it is used to prevent any change in the pH of a solution. Buffer solutions are used in protein formulations as a means of keeping proteins stable within a narrow pH range.

The buffer of this invention has a pH in the range from about 6.0 to about 6.6, more preferably in the range from about pH 6.0 to about 6.3. Examples of buffers that will control the pH in this range include phosphate, citrate-phosphate, succinate (such as sodium succinate), gluconate, histidine, citrate, maleate, tris-maleate, tris, and other organic acid buffers. As used herein the term "excipient" is intended to mean a therapeutically inactive substance. Excipients are included in a formulation for a wide variety of purposes, for example, as a buffer, stabilizer, tonicity agent, surfactant, anti-oxidant, cryoprotectant or diluent.

Suitable excipients include, but are not limited to, polyols (also known as sugar alcohols) such as mannitol or sorbitol, sugars such as sucrose, lactose or dextrose, salts such as NaCl, KCl or calcium phosphate, amino acids, for example, histidine, lysine, aspartic acid, or glutamic acid, surfactants, as well as saline and water. The purity of the excipient should meet compendial standards (e.g., USP, EP, JP) and be of sufficient purity for subcutaneous, intramuscular, or intravenous injection into humans.

Various literature references are available to facilitate selection of pharmaceutically acceptable carriers or excipients. See, e.g., Remington's Pharmaceutical Sciences and U.S. Pharmacopeia: National Formulary, Mack Publishing Company, Easton, Pa. (1984); Hardman et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman et al. (eds.) (1990) Pharmaceutical Dosage Forms: Disperse Systems, Marcel Dekker, NY; Weiner, Wang, W., Int. J. Pharm. 185:129-188 (1999) and Wang, W., Int. J. Pharm. 203:1-60 (2000), and Kotkoskie (2000) Excipient Toxicity and Safety, Marcel Dekker, Inc., New York, N.Y.

As used herein the term "tonicity agent" refers to an agent which functions to render a solution similar in osmotic characteristics to physiologic fluids. For example, Dextrose, Mannitol, Sodium Chloride, Potassium chloride and Glycerin are typically used in protein formulations as tonicity agents to render the parenteral product solutions "isotonic" with body fluids.

The term "isotonic" means that the formulation of interest has essentially the same osmotic pressure as human blood. Isotonic or physiologic formulations will generally have an osmotic pressure from about 270-328 mOsm. Slightly hypotonic pressure is 250-269 and slightly hypertonic pressure is 328-350 mOsm. Osmotic pressure can be measured, for example, using a vapor pressure or ice-freezing type osmometer. Typically, particular excipients, referred to in the field as "tonicity modifiers" or "tonicity agents" are used to control the tonicity of a pharmaceutical formulation. Salts (NaCl, KCl, MgCl2, CaCl2, etc.) represent commonly used as tonicity modifiers. In addition, excipients such as, but not limited to, sucrose, mannitol, glycine etc. can function as tonicity modifiers.

"Pharmaceutically acceptable" excipients (vehicles, additives) are those which can reasonably be administered to a subject mammal to provide an effective dose of the active ingredient employed.

The term "aggregates", as used herein, is meant to refer to protein aggregates. It encompasses multimers (such as dimers, tetramers or higher order aggregates) of the Fc-fusion protein to be purified and may result, e.g., in high molecular weight aggregates.

The aggregate content can be determined using High Performance Size Exclusion chromatography (HP-SEC), which separates molecules based on size. The early eluting peak corresponds to high molecular weight species or % aggregates. The main peak (intact protein) corresponds to % monomer. The late eluting peak corresponds to low molecular weight species or % fragments.

As used herein, the term "misfolded Fc-Fusion protein" refers to Fc-Fusion proteins that are incorrectly or improperly folded thus altering the three-dimensional structure. Misfolds can also encompass the term "aggregate". However, aggregates do not necessarily have to be misfolds.

As used herein, the phrase "stable" as it is used herein to refer to pharmaceutical compositions/formulations is a term of art and is used herein in accordance with its established meaning. In general the term refers to a composition in which a biopharmaceutical protein retains the physical, chemical and biological properties required by a regulatory agency for its approval. For example, a stable pharmaceutical composition is a formulation that between the time that is made and the time that it is used (or reaches the end of its intended shelf-life), does not undergo any changes in its physical, chemical or biological properties which renders it unsafe or ineffective for its intended pharmaceutical use. The meaning of the term is illustrated by the standards established in ICH Q5C, "Quality of Biotechnological Products: Stability Testing of Biotechnological/Biological Products," by the International Conference on Harmonization of Technical Requirements of Pharmaceuticals for Human Use, which is herein in incorporated by reference, particularly in parts pertinent to the stability of pharmaceutical compositions. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and ones, A. Adv. Drug Delivery Rev. 10:29-90 (1993). In practice, stability can be measured at a selected temperature for a selected time period.

A "stable" biosimilar etanercept formulation is a pharmaceutical formulation with no significant changes observed at a refrigerated temperature of (2-8° C.) for at least 3 months, preferably 6 months, and more preferably 1 year, and even more preferably up through 2 years. Stability of the formulations disclosed herein can be evaluated using the following criteria: 1) the aqueous formulation is colorless, or clear to slightly opalescent by visual analysis; 2) the protein content is between 47.0 to 53.0 mg·mL; 3) the pH is maintained within +/−0.2 pH units from target pH; 4) the percent intact protein (% monomer) by SEC is ≥96%; 5) the percent main peak (Peak 2) as measured by HIC-HPLC is ≥87.5% and the percent Peak 1 is ≤12.5%; 6) the relative potency based on ELISA is within 70-150%.

A fusion protein "retains its biophysical stability" in a pharmaceutical formulation if it shows no significant increase of aggregation, precipitation and/or denaturation upon visual examination of color and/or clarity, or as measured by UV light scattering, size exclusion chromatography (SEC) and dynamic light scattering. The changes of protein conformation can be evaluated by fluorescence spectroscopy, which determines the protein tertiary structure, and by FTIR spectroscopy, which determines the protein secondary structure.

As used herein the term "opalescence" refers to an optical phenomenon that arises from multiple scattering events of visible light by solutes present in a solution. Moderate to high concentrations of protein solutions often exhibit opalescence or mild form of turbidity due to scattering of visible light.

A fusion protein "retains its biochemical stability" in a pharmaceutical formulation, if it shows no significant chemical alteration. Chemical stability can be assessed by detecting and quantifying chemically altered forms of the protein. Degradation processes that often alter the protein chemical structure include hydrolysis or clipping (evaluated by methods such as size exclusion chromatography and SDS-PAGE), oxidation (evaluated by methods such as by peptide mapping in conjunction with mass spectroscopy or MALDI/TOF/MS), deamidation (evaluated by methods such as ion-exchange chromatography, capillary isoelectric focusing, peptide mapping, isoaspartic acid measurement), and isomerization (evaluated by measuring the isoaspartic acid content, peptide mapping, etc.).

A fusion protein "retains its biological activity" in a pharmaceutical formulation, if the biological activity of the fusion protein at a given time is within a predetermined range of the biological activity exhibited at the time the pharmaceutical formulation was prepared. The biological activity of a etanercept can be determined, for example, by a TNF binding assay. Specifically, an ELISA (enzyme-linked immunosorbent assay) is used to directly measure the interactions of etanercept and TNF-α extracellular domain. The assay is run in a direct binding manner such that a constant amount of TNF-α is adsorbed onto a 96 well plate, after which etanercept sample is serially diluted across the plate to allow the binding between varying amounts of sample in solution to the fixed amount of TNF-α on the plate. Another potency assay which can be used is a cell-based assay. A cell-based assay is a functional in-vitro potency assay which measures biological activity. In this instance, the ability of etanercept to neutralize 50% apoptosis in the presence of A375 cells is translated into potency units.

Once a formulation is prepared as described herein, stability of the biosimilar etanercept protein can be assessed using methods known in the art, including but not limited to size exclusion chromatography, cation chromatography, particle counting and in vitro binding and/or functional assays. Generally speaking biochemical and/or physiochemical activity can be assessed at two or more time points to determine the stability of the etanercept in the formulation. It should be noted that the retention of structure and/or function and/or biological activity does not have to be 100%. Measurement of the stability of a formulation is a comparative exercise.

Therefore, if one formulation is said to be more stable, or have greater stability than another, the formulation with the greater stability has retained a higher percentage of a desired structural or functional characteristic that the other formulation(s). For example, formulation A is more stable than formulation B if it maintains a greater percentage of the main peak when measured by size exclusion chromatography (i.e., it is characterized by a lower degree of aggregation).

The formulations disclosed herein were selected in accordance with a defined set of criteria developed to ensure that the safety, purity, and potency of a biosimilar drug product comprising etanercept would be highly similar to the corresponding features of the reference product. For example, the optimal pH, buffer system and excipients were selected on the basis of biochemical stability data collected from accelerated stability studies primarily on the basis of minimizing the change in opalescence; minimizing the percentage of aggregates and fragments; and maximizing the percentage of monomer. HIC-HPLC data was used as an orthogonal method to SEC-HPLC to monitor changes in percent aggregate. Data from intrinsic fluorescence and light scattering studies was also utilized to corroborate primary selection criteria described above.

In some embodiments, stability of a formulation includes, for example retention of biological activity. Biological activity can be assessed using, for example an in vitro, in vivo and/or in situ assay indicative of the biopharmaceutical's function. Retention of stability of a biopharmaceutical in a formulation of the invention can include, for example, retention of activity between 80 and about 100% or more, depending on the inherent variability in the assay. For example, retention in stability can include retention of activity between about 80% to about 99% or between about 85% to about 95% compared to the activity of the biopharmaceutical at an initial time point. Generally speaking, an initial time point is selected to be the time that a biopharmaceutical is first prepared in a formulation or first examined for quality (for example a determination of if it meets release specifications).

As used herein the term "potency" refers to the specific ability or capacity of the product, as indicated by appropriate laboratory tests, to yield a given result. In the case of biologics, potency will help establish structure-function correlations, assist in determining immunologic response, and elucidate the molecule's biological identity.

As used herein the term "accelerated stability study" refers to a stability study conducted under conditions (e.g., 37° C. or 40° C. temperature) designed to increase the rate of chemical degradation or physical change of a Drug Substance (DS)/Active Pharmaceutical Ingredient (API) or Drug Product (DP) using exaggerated storage conditions. The purpose of the study is to monitor any degradation reactions which than will help to predict the shelf life of a Drug Substance (API) or Drug Product (DP) under the defined storage conditions.

The "isoelectric point" or "pI" of a protein is the pH at which the protein has a net overall charge equal to zero, i.e. the pH at which the protein has an equal number of positive and negative charges. Determination of the pI for any given protein can be done according to well-established techniques, such as e.g. by isoelectric focusing. Isoelectric focusing is a technique for separating different molecules by differences in their isoelectric point (pI). It is a type of zone electrophoresis, usually performed on proteins in a gel, that takes advantage of the fact that overall charge on the molecule of interest is a function of the pH of its surroundings.

As used herein, "shelf life" means that the storage period during which an active ingredient such as a therapeutic protein in a pharmaceutical formulation has minimal degradation (e.g., not more than about 2-3% degradation) when the pharmaceutical formulation is stored under specified storage conditions, for example, 2-8° C.

Throughout this application, various publications (including patents and patent applications) are referenced. The disclosures of these publications in their entireties are hereby incorporated by reference. The references cited in the present application are not admitted to be prior art to the claimed invention.

Analytical methods suitable for evaluating the product stability include size exclusion chromatography (SEC), dynamic light scattering test (DLS), differential scanning calorimetery (DSC), iso-asp quantification, potency, UV at 340 nm, UV spectroscopy, and FTIR. SEC (J. Pharm. Scien., 83:1645-1650, (1994); Pharm. Res., 11:485 (1994); J. Pharm. Bio. Anal., 15:1928 (1997); J. Pharm. Bio. Anal., 14:1133-1140 (1986)) measures percent monomer in the product and gives information of the amount of soluble aggregates. DSC (Pharm. Res., 15:200 (1998); Pharm. Res., 9:109 (1982)) gives information of protein denaturation temperature and glass transition temperature. DLS (American Lab., November (1991)) measures mean diffusion coefficient, and gives information of the amount of soluble and insoluble aggregates. UV at 340 nm measures scattered light intensity at 340 nm and gives information about the amounts of soluble and insoluble aggregates. UV spectroscopy measures absorbance at 278 nm and gives information of protein concentration. FTIR (Eur. J. Pharm. Biopharm., 45:231 (1998); Pharm. Res., 12:1250 (1995); J. Pharm. Scien., 85:1290 (1996); J. Pharm. Scien., 87:1069 (1998)) measures IR spectrum in the amide one region, and gives information of protein secondary structure.

Techniques for assessing degradation vary depending upon the identity of the protein in the pharmaceutical formulation. Exemplary techniques include size-exclusion chromatography (SEC)-HPLC to detect, e.g., aggregation, reverse phase (RP)-HPLC to detect, e.g. protein fragmentation, ion exchange-HPLC to detect, e.g., changes in the charge of the protein, mass spectrometry, fluorescence spectroscopy, circular dichroism (CD) spectroscopy, Fourier transform infrared spectroscopy (FT-IR), and Raman spectroscopy to detect protein conformational changes. All of these techniques can be used singly or in combination to assess the degradation of the protein in the pharmaceutical formulation and determine the shelf life of that formulation.

The pharmaceutical formulations of the present invention preferably exhibit degradation (e.g., fragmentation, aggregation or unfolding) of not more than about 2 to about 5% over a period of 2-3 years stored at refrigerated conditions of 2-8° C.

As used herein the term "about" is understood to mean that there can be variation in the concentration of a component of the described formulation which can encompass a range from 5%, 10%, 15% or up to and including 20% of the given value. For example, if a formulation has about 25 mg of an excipient, it may include an amount ranging from 20 mg to 30 mg.

It should be understood that while various embodiments are presented using "comprising" language, under various circumstances, a related embodiment may also be described using "consisting of" or "consisting essentially of" language. The phrase "consists essentially of," or variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition.

It should be understood that when describing a range of values, the characteristic being described could be an individual value within the range. For example, "a pH from about pH 4 to about pH 6," should not be construed to mean that the pH of a formulation in question varies 2 pH units in the range from pH 4 to pH 6 during storage, but rather a value may be picked in that range for the pH of the solution, and the pH remains buffered at about that pH.

Etanercept is a tumor necrosis factor-α inhibitor which binds to both soluble and membrane-bound TNF-α (US Full Prescribing Information 2006). It inhibits the action of TNF by competitively binding to either TNF-α and/or lymphotoxin-α, thereby preventing TNF from binding to endogenous receptors located on the cell surface. The dimeric structure of etanercept, which confers antibody-like structural properties and promotes covalent oligomerization, increases its apparent affinity and makes it a 50- to 100-fold more potent binder of TNF-α than the endogenous soluble receptor TNF-α receptor (Goffe and Cather, *J. Am. Acad. Dermatol.* 49:S105 (2003)) TNF-α which circulates in its soluble form is primarily produced by macrophages and to a lesser extent by T cells. Linkage of the receptor to the Fc portion of human IgG1 also substantially prolongs the half-life of etanercept relative to the half-life of endogenous soluble forms of the TNF-α receptor (Goffe and Cather, *J. Am. Acad. Dermatol.* 49:S105 (2003)).

Etanercept modulates biologic responses that are initiated or controlled by the proinflammatory cytokine TNF-α, including, but not limited to, expression of adhesion molecules and serum levels of other inflammatory mediators and matrix metalloproteinase. It exerts its therapeutic effect by binding to and inactivating both tumor necrosis factor (TNF) and lymphoxin-alpha. Etanercept competitively inhibits the interaction of TNF with cell surface receptors and binds to soluble TNF in vivo, thereby prevent TNF-mediated cellular responses. In the United States, etanercept is approved for moderate to severe active rheumatoid arthritis (as monotherapy or as combination therapy with methotrexate), active psoriatic arthritis, chronic moderate to severe plaque psoriasis, moderate to severe active polyarticular juvenile arthritis, and active ankylosing spondylitis.

The recommended dose for etanercept in the United States is 50 mg once weekly in adults with rheumatoid arthritis (Dore, R. K., et al., *Clin. Exp. Rheumatol.* 2007 25(1) pp. 40-46) ankylosing spondylitis, and psoriatic arthritis. In psoriasis patients, the dose is 50 mg twice weekly for three months followed by 50 mg once weekly. The recommended dose for pediatric patients with rheumatoid arthritis is 0.8 mg/kg per week (US Full Prescribing Information 2006).

After subcutaneous administration, etanercept takes approximately 2 days (about 48 hours) to reach maximum concentration (Cmax), and terminal half-life is approximately 3 to four days (Sullivan, J et al. (2006) J. Clinical Pharmacol., 46:654-661). The absolute availability of subcutaneous etanercept has been reported as 58% (Zhou, H et al. (2004) Int. J. Clin. Pharm. Ther. 42:267-276).

Etanercept (ENBREL, Pfizer/Amgen) is available as 25-mg multiple dose vials of lyophilized power for reconstitution, as well as a 1 ml prefilled syringe containing 50 mg etanercept for single use, and an autoinjector containing 50 mg etanercept for single use. The 50 mg/mL liquid formulation of etanercept supplied in prefilled syringes was developed to enhance caregiver convenience and patient adherence to treatment regimens. The solution of etanercept in the single-use prefilled syringe and the single-use prefilled Sure-Click® autoinjector is sterile, clear and colorless, preservative-free, and is formulated at pH 6.3±0.2. As indicated in Table 1 the liquid solution comprises 25 mM L-arginine hydrochloride as an excipient, which according to '702, functions as an aggregation inhibitor.

ENBREL is also supplied in a multiple-use vial as a sterile, white, preservative-free, lyophilized powder. Reconstitution with 1 mL of the supplied bacteriostatic water for injection, USP (containing 0.9% benzyl alcohol) yields a multiple-use, clear and colorless solution with a pH of 7.4±0.3. Table 1 summarizes the etanercept concentrations and excipients present in the lyophilized powder and aqueous formulations.

TABLE 1

| Format | Active Ingredient | Excipients |
| --- | --- | --- |
| Prefilled Syringe SureClick® Autoinjector | 0.98 ml of a 50 mg/mL solution of etanercept | 1% sucrose<br>100 mM sodium chloride<br>25 mM L-arginine hydrochloride<br>25 mM sodium phosphate |
| Multi-use vial | 25 mg of etanercept | 40 mg mannitol<br>10 mg sucrose<br>1.2 mg tromethamine |

U.S. Pat. No. 7,648,702 (Stable Aqueous Formulation of a Soluble TNF Receptor and Arginine) (referred to herein as the '702 patent, equivalent of EP 1478394B and WO 2003/072060) (assigned to Immunex Corporation) discloses liquid formulations suitable for long-term storage of etanercept. The '702 patent discloses the use of the amino acids L-arginine and/or L-cysteine act to reduce aggregation of Fc domain containing proteins in a liquid formulation. In a particular embodiment, L-arginine at a concentration from about 10 mM to about 200 mM is used to inhibit the aggregation of etanercept in an aqueous pharmaceutical composition. Aggregation inhibitors reduce a polypeptide's tendency to associate in inappropriate or unwanted ternary or quaternary complexes.

The pharmaceutical compositions disclosed in the '702 patent optionally comprise a buffer which maintains the composition pH at a range of about 6.0 to about 7.0, a tonicity modifier and one or more other excipients. A tonicity modifier is described to be a molecule that contributes to the osmolality of a solution. The osmolality of a pharmaceutical composition is preferably regulated in order to maximize the active ingredient's stability and also to minimize discomfort to the patient upon administration.

One illustrative embodiment disclosed in the '702 patent describes a pharmaceutical composition comprising about 25 to about 50 mg TNFR:Fc (etanercept, active ingredient), about 10 mM to about 100 mM L-arginine, about 10 mM to about 50 mM sodium phosphate, about 0.75% to about 1.25% sucrose, about 50 mM to about 150 mM NaCl, at about pH 6.0 to about pH 7.0. In another embodiment, the '702 patent discloses that the L-arginine can be replaced with L-cysteine (at about 1 to about 500 micromolar) as an aggregation inhibitor in the pharmaceutical compositions.

The US Food and Drug Administration (FDA) and the European Medicines Agency (EMA) have published draft guidelines indicating a willingness to approve biosimilar drug products that have a different formulation than its reference product, provided that the licensing application contains sufficient information to establish that the biosimilar product is "highly similar" to the reference product notwithstanding minor differences in clinically inactive components. In addition, biosimilar applicants will also have to satisfy the prong of the comparability assessment that requires proof that there are no clinically meaningful differences between the biosimilar product and the reference product in terms of safety, purity, and potency (FDA Biosimilar Draft Guidance: Questions and Answers Regarding Implementation of the Biologics Price Competition and Innovation Act of 2009, Part I Biosimilarity or Interchangeability, Q.I.3). The EMA has commented that the applicant "should take into account state-of-the-art technology and, regardless of the formulation selected, the suitability of the proposed formulation with regards to stability, compatibility (i.e. interaction with excipients, diluents and packaging materials), integrity, activity and strength of the active substance should be demonstrated" (Guideline on similar biological medicinal products containing biotechnology-derived proteins as active substance: quality issues (draft, revision 1) EMA/CHMP/BWP/247713/2012).

To date, there are no established criteria describing how the Food and Drug Administration (FDA) will require a biosimilar applicant to establish that a particular biopharmaceutical product is "highly similar" to a reference product. The statutory definition provides that a biosimilar product can have minor differences in clinically inactive components, provided that "there are no clinically meaningful differences between the biological product and the reference product in terms of the safety, purity, and potency of the product" (42 USC §262(i)(1)). An "inactive ingredient" is any component of a drug product other than the active ingredient. In practice excipients and stabilizers are inactive ingredients of pharmaceutical compositions. In the absence of guidance from the regulatory authorities, it is not clear if the "highly similar" standard will tolerate the same types of differences in quality attributes as the comparability standard. However, it is clear that there is a need for alternative pharmaceutical compositions comprising etanercept prepared in alternative formulations.

Biopharmaceutical proteins such as TNFR:Fc are typically produced by culturing suitable host/vector systems to express the recombinant translation products of the DNAs encoding the same, which are then purified from culture media or cell extracts. Various mammalian cell culture systems are advantageously employed to fusion proteins and monoclonal antibodies because expression of recombinant proteins in mammalian cells because mammalian cell secretory pathways are known to facilitate the assembly and folding of biologically active proteins.

In order to create soluble, secreted Fc-fusion proteins, that are released into the cell culture supernatant, either the natural signal peptide of the therapeutic moiety of the Fc-fusion protein is used, or preferably a heterologous signal peptide, i.e., a signal peptide derived from another secreted protein being efficient in the particular expression system used. If the Fc-fusion protein to be purified is expressed by mammalian cells secreting it, the starting material of the purification process of the invention is cell culture supernatant, also called harvest or crude harvest. If the cells are cultured in a medium containing animal serum, the cell culture supernatant also contains serum proteins as impurities.

In accordance with the present invention, the recombinant Fc-fusion protein can be produced in eukaryotic expression systems, including mammalian cells and glycoengineered yeast cells, resulting in glycosylated Fc-fusion proteins. Preferably, the Fc-fusion protein expressing and secreting cells are cultured under serum-free conditions. The Fc-fusion protein may also be produced in a chemically defined medium. Typically, the starting material of the purification process of the invention is serum-free cell culture supernatant that mainly contains host cell proteins as impurities.

In accordance with the present invention there may be employed conventional molecular biology, microbiology, protein expression and purification, antibody, and recombinant DNA techniques within the skill of the art. Such techniques are explained fully in the literature. See, e.g., Sambrook et al. (2001) *Molecular Cloning: A Laboratory Manual*. 3$^{rd}$ ed. Cold Spring Harbor Laboratory Press: Cold Spring Harbor, N.Y.; Ausubel et al. eds. (2005) *Current Protocols in Molecular Biology*. John Wiley and Sons, Inc.: Hoboken, N.J.; Bonifacino et al. eds. (2005) *Current Protocols in Cell Biology*. John Wiley and Sons, Inc.: Hoboken, N.J.; Coligan et al. eds. (2005) *Current Protocols in Immunology*, John Wiley and Sons, Inc.: Hoboken, N.J.; Coico et al. eds. (2005) *Current Protocols in Microbiology*, John Wiley and Sons, Inc.: Hoboken, N.J.; Coligan et al. eds. (2005) *Current Protocols in Protein Science*, John Wiley and Sons, Inc.: Hoboken, N.J.; and Enna et al. eds. (2005) *Current Protocols in Pharmacology*, John Wiley and Sons, Inc.: Hoboken, N.J.; *Nucleic Acid Hybridization*, Hames & Higgins eds. (1985); *Transcription And Translation*, Hames & Higgins, eds. (1984); *Animal Cell Culture* Freshney, ed. (1986); *Immobilized Cells And Enzymes*, IRL Press (1986); Perbal, *A Practical Guide To Molecular Cloning* (1984); and Harlow and Lane. *Antibodies: A Laboratory Manual* (Cold Spring Harbor Laboratory Press: 1988).

In practice, CHO cell lines are typically the production cell line of choice because they offer well-characterized, selectable and amplifiable gene expression systems which facilitate high level recombinant protein expression in these cells (Kaufman, R. J., *Meth. Enzymol.* 185:527-566 (1990)). In addition, these cells are easy to manipulate as adherent or suspension cultures and exhibit relatively good genetic stability. CHO cells and recombinant proteins expressed in them have been extensively characterized and have been approved for use in clinical manufacturing by regulatory agencies.

However, as expression systems and vectors have been improved to maximize levels of expression from eukaryotic hosts, not all of the recombinant protein expressed and secreted from these hosts is in the desired, most active conformation. Generally speaking, the desired conformation for a recombinant protein is the three-dimensional structure of a protein that most closely resembles, and/or duplicates the function of, the naturally occurring domain of that protein. TNFR:Fc (i.e., etanercept) comprises 7 disulfide bonds in the Fc region and 22 disulfide bonds in the TNF receptor region of the protein. Accordingly, there is a high probability of disulfide scrambling during a commercial bioprocessing protocol.

U.S. Pat. No. 7,157,557 (referred to herein as the '557 patent) discloses that not all of the soluble form of the human TNF receptor fused to an Fc domain of a human immunoglobulin protein (TNFR:Fc) protein that is expressed by mammalian cells is correctly folded into a native tertiary conformation. More specifically, the '557 patent discloses that the p75 TNFR:Fc (i.e., etanercept) produced by CHO cell culture elutes off a hydrophobic interaction column (HIC) as three distinct peaks, denoted therein as fraction #1, fraction #2 and fraction #3. The '557 patent discloses that Fraction #1 comprises TNFR:Fc fragments, Fraction #2 comprises properly folded TNFR:Fc (which is the desired fraction), and Fraction #3 comprises misfolded disulfide scrambled TNFR:Fc variants and aggregated protein product (see FIG. 1 of the '557 patent). It is further disclosed that Fraction #3, which is characterized by low TNF biding activity and bioactivity in comparison to fraction #2, can comprise from 20 to 60% of the protein. The '557 patent discloses a method for increasing the recovery of active TNFR:Fc having a desired conformation from mammalian cell culture which comprises contacting a preparation of etanercept produced by mammalian cell culture with a reduction/oxidation coupling reagent at a pH of about 7 to 11.

U.S. Pat. No. 7,294,481 (referred to herein as the '481 patent) further teaches that fraction #1 represents truncated forms arising from proteolytic cleavage, and that fraction #3 comprises a heterogenous mixture comprised of misfolded product along with other process related impurities. The '481 patent discloses that the misfolded TNFR:Fc is formed early in the cell culture process and confirms that fraction #3, which comprises a heterogeneous mixture of molecular forms, can represent a significant proportion (i.e., 25-50%) of the expression product. Based on the data included in the '481 patent it appears as if the TNFR:Fc in fraction #3 contains localized, scrambled disulfides. It is concluded that this would almost certainly result in a more hydrophobic molecule with an incorrect conformation characterized by increased HIC increased retention. SDS-PAGE results indicate that peak #3 contains a mixture of intact TNFR:Fc, TNFR:Fc fragments and nearly all of the aggregated TNFR: Fc present in the expression product.

The '481 patent provides an alternative approach to dealing with the heterogeneity of etanercept expression products by modifying aspects of the cell culture conditions in order to reduce the production of said misfolded TNFR: Fc. More specifically, the '481 patent suggests the use of culture conditions wherein the host cells are maintained at a temperature of 28-34° C. during the production phase in the presence of an alkanoic acid.

Etanercept is a glycoprotein which comprises several O-glycan sites in the receptor portion of the fusion protein as well as the IgG1-specific N-glycosylation sites present in the Fc portion of the molecule. Glycosylation is one of the most common posttranslational modifications that occur during the production of a recombinant Fc-fusion protein using mammalian cell lines. Glycosylation can affect protein activity, solubility, stability and immunogenicity. Glycosylated proteins, such as monoclonal antibodies and Fc-containing fusion proteins are complex molecules and even a well-controlled product can consist of several hundred or more glycoforms characterized by having the same amino acid sequence but distinct glycan profiles (*Nature Biotechnology* 29(4):310 (2011)). Different glycoforms frequently have different physical and chemical properties.

The most common site of glycosylation in antibodies and Fc-fusion proteins is through N-linkage of the Asn 297 side chain on the CH2 domain of the immunoglobulin heavy chain. The presence of oligosaccharides at the CH2 N-glycosylation site is known to affect the pharmacological and biological properties of Fc-containing proteins. The final glycan profile of a biopharmaceutical glycoprotein is influenced by the production host cell, the culture conditions and the purification processes used to manufacture the product.

Regulatory authorities assume that each therapeutic protein has a unique and specific set of structural features (e.g., amino acid sequences, glycosylation profile, and folding) that are essential to their intended effect, and that even slight modifications can affect their immunogenicity and/or clinical efficacy. Therefore, it is not surprising that changes in manufacturing process used to produce an approved biopharmaceutical are tightly regulated by health authorities. When the manufacturer of a biopharmaceutical product changes its manufacturing process regulatory agencies will require the manufacturer to perform a comparability exercise comparing the quality of products produced using the pre- and post-change manufacturing processes. The exercise will usually include data collected from both physiochemical and functional assays.

The principles of the comparability exercise are established in guidelines such as the International Conference on Harmonization (ICH) Q5E which indicates that "the demonstration of comparability does not necessarily mean that the quality attributes of the pre-change and post-change product are identical, but that they are highly similar and that the existing knowledge is sufficiently predictive to ensure that any differences in quality attributes have no adverse impact upon safety or efficacy" (*Nature Biotechnology*, 29(4):310 (2011)). Generally speaking, health authorities and companies tolerate some degree of drift in a manufacturing process, provided that it does not alter the safety or efficacy of the product.

Investigators at Sandoz Biopharmaceuticals have published data intended to provide insight into the level of variation in the glycosylation profile and N- and C-terminal heterogeneity of etanercept which regulatory authorities tolerate (*Nature Biotechnology*, 29(4):310 (2011)). The study used glycan mapping and cation exchange chromatography (CEX) to characterize the quality attributes of etanercept present in commercial batches, sourced in the European Union and the United States, and marketed in the above-referenced commercial formulation (Table 1). The results illustrate major differences in the glycosylation profile (i.e., the amount of variants containing the N-glycan G2F decreased from approximately 50% in the pre-change batch to approximately 30% in the post-change batch samples). In addition, CEX analysis showed a change in the amount of basic variants, which corresponds primarily to C-terminal lysine variants from 15-30% in the pre-change to 40-60% in the post-change batch (see FIG. 3 on page 312 of *Nature Biotechnology*, 29(4):310 (2011)). The authors note that etanercept sourced from the same commercial batches as the test samples remained on the market with unaltered labels during the tested time frame, which supports an inference that the regulatory authorities consider the documented changes as not likely to result in an altered clinical profile.

Chemical and/or charge heterogeneity involves a modification of the primary sequence of the mAb or Fc-fusion protein. Common alterations which can occur during the manufacture of a biological drug substance include changes to the disulfide bonds, modifications in N-glycosylation, C-terminal lysine processing, glycosylation of Lys residues, deamidation, isomerization, oxidation, and hydrolysis/fragmentation. Oxidative attack on proteins results in site-specific amino acid modifications, fragmentation of the peptide chain, aggregation of cross-linked reaction products, disulfide bond reshuffling (leading to misfolding), altered electrical charge and increased susceptibility to proteolysis. The amino acids in a peptide differ in their susceptibility to attack, and the various forms of activated oxygen differ in their potential reactivity. Primary, secondary, and tertiary protein structures alter the relative susceptibility of certain amino acids. Sulphur containing bridges such as those in etanercept, and thiol groups specifically, are very susceptible sites. Activated oxygen can abstract an H atom from cysteine residues to form a thiyl radical that will cross-link to a second thiyl radical to form disulphide bridges. Alternatively, oxygen can add to a methionine residue to form methionine sulphoxide derivatives.

Conformational heterogeneity relates to the distribution of the conformational states as defined by the intrinsic thermodynamic stability of a mAb or fusion protein under a given solution condition (Sharma, V., "The Formulation and Delivery of Monoclonal Antibodies", *Therapeutic Monoclonal Antibodies*, John Wiley & Sons (2009)). Typically a protein's native conformation is defined as the one that is prevalent under physiological conditions. Altered non-native conformations may be produced during the cell culture process as a result of misfolding, or may occur under different solution conditions ('557 patent). The non-native variants may be characterized by a different stability profile (i.e., more or less prone to aggregation or fragmentation), or be less biologically active. In practice, spectroscopic techniques, such as circular dichroism spectroscopy, differential scanning calorimetry and fluorescence spectroscopy can be used to determine the conformational heterogeneity of a protein composition which provides insight into the conformational stability of the composition.

Determining the conformation of a protein, and the relative proportions of a conformation of a protein in a mixture, can be done using any of a variety of analytical and/or qualitative techniques. If the two conformations resolve differently during chromatography, electrophoresis, filtering or other purification technique, then the relative proportion of a conformation in the mixture can be determined using such purification techniques. For example, in the non-limiting embodiments described below, at least two different conformations of TNFR:Fc could be resolved by way of hydrophobic interaction chromatography. Further, since far-UV Circular Dichroism has been used to estimate secondary structure composition of proteins (Perczel, et al., *Protein Engrg.* 4:669-679 (1991)), such a technique can determine whether alternative conformations of a protein are present. Still another technique used to determine conformation is fluorescence spectroscopy which can be employed to ascertain complimentary differences in tertiary structure assignable to tryptophan and tyrosine fluorescence. Other techniques that can be used to determine differences in conformation and, hence, the relative proportions of a conformation, are on-line SEC to measure aggregation status, differential scanning calorimetry to measure melting transitions (Tm's) and component enthalpies, and chaotrope unfolding.

Size heterogeneity can be primarily attributed to fragmentation and aggregation. Protein aggregation is a common problem in bioprocessing and can occur during expression, purification or storage. Aggregation is a particular challenge in downstream processes designed for the purification of Fc-fusion preparations which contain high levels of high molecular weight species; and is dependent on experimental variables such as, the amino acid sequence of the protein, the complexity of the protein, temperature, pH, and the type of ion present in a buffer and the buffer's ionic strength.

Aggregation is a general term that encompasses several types of interactions or characteristics. Usually aggregation results from intermolecular associations of partially denatured protein chains, however, it may also result from chemical degradation and subsequent exposure of hydrophobic surfaces or from disulfide bond scrambling. Protein aggregates can arise from several mechanisms and may be classified in numerous ways, including soluble/insoluble, covalent/noncovalent, reversible/irreversible, and native/denatured. Because the term "aggregate" encompasses heterogeneous species ranging from soluble dimers to visible particles comprising millions of monomers, it is difficult to exactly measure, characterize and quantify. In addition, although there are clear guidelines regarding the number of particles ≥10 µm and ≥25 µm in size that may be present in a pharmaceutical composition, the level of soluble aggregates (i.e., dimers and trimers which are not visible as discrete particles and which are not removed by a filter with a pore size of 0.22 µm) that are acceptable are not well defined.

Aggregation is one of the major challenges encountered during the development of a manufacturing process for an Fc-fusion protein. Throughout production, the protein solution is pumped, stirred, and filtered and encounters numerous containers made of different materials. All of these factors can potentially promote the formation of aggregates. For example, during cell culture, the protein is secreted from the cell into culture medium containing the cells, ions, nutrients for the cells, host cell proteins (including proteases), dissolved oxygen, and other species. The resulting cell culture fluid is harvested and purified over a variety of chromatography resins (e.g., protein A, and anion or cation exchange resins) which may involve the use of acidic, or high pH and/or high ionic strength elution buffers. Finally, the protein is formulated using ultrafiltration/diafiltration. The formulated protein may be stored frozen for some period of time before being filled into its final container.

The accumulation of high levels of protein during cell culture can promote intracellular aggregation attributed to either the interactions of unfolded protein molecules or to inefficient recognition of the nascent polypeptide chain by molecular chaperones required for proper folding. In addition, secretion of the biopharmaceutical protein into the cell culture media exposes the protein to unfavorable conditions. However, it is possible to influence the amount of aggregates produced during the upstream unit operations required to manufacture a biopharmaceutical protein by carefully selecting the expression system and cell culture conditions. For example, the culture temperature can be shifted during the production phase, or components can be added to the growth or feed media to influence the ability of the expressed protein to fold into a native structure.

Because association between two or more antibody molecules is a prerequisite for aggregation, the process is often concentration dependent. Depending upon the mechanism driving the association, a variety of aggregates may be formed. Some aggregates are formed due to a tendency for self-association, which is concentration dependent process that can be reversible upon dilution. Fc-containing proteins, either mAbs or fusion proteins, can form covalent irreversible aggregates through intermolecular disulfide cross-links ('557 patent). In CHO cells, disulfide bonds formation occurs after the nascent polypeptide is translocated to the lumen of the endoplasmic reticulum (ER). Proper disulfide bond formation is critical for folding etanercept into its native conformation. Formation of disulfide bonds typically require an oxidative environment. In the absence of this environment, free thiols on the cysteines may remain unpaired, leading to improper folding.

Aggregation, or size heterogeneity, can alter not only the therapeutic, pharmacokinetic and pharmacodynamics profiles of the therapeutic protein, but also has a negative impact on the safety profile, because it is considered a strong risk factor for immunogenicity. Therefore, it is well established that aggregation of biopharmaceutical proteins is undesirable as it may result in immunogenicity (Cleland, et al., *Crit. Rev. Therapeutic Drug Carrier Systems,* 10:307 (1993)). Aggregation of proteins may either reveal new epitopes or leads to the formation of multivalent epitopes, which may stimulate the immune system. Factors, which could be considered to contribute to aggregate formation, include formulation, purification processes, viral inactivation procedures and storage conditions of intermediates and finished product. For protein therapeutics, the presence of aggregates of any type is typically considered to be undesirable because of the concern that the aggregates may lead to an immunogenic reaction (small aggregates) or may cause adverse events on administration (particulates) (Cromwell, M. E., et al., *Protein Aggregation and Bioprocessing, AAPS Journal.* 8(3): E572 (2006)).

Chemical degradation represents one of the major degradation pathways of Fc-containing proteins. It is well known that chemical degradation pathways often exhibit a pH dependence. For example, solution environments of higher than pH 7.0 can promote protein deamidation of the asparagine residues, disulfide exchange and aggregation, while lower pH values (e.g., pH 4.0 and below) can promote isomerization, hydrolysis and fragmentation. In addition, because pH can have an impact on the tertiary conformation and net charge of a protein, physical aggregation can also exhibit a pH dependence.

During the manufacture of biologics, a protein molecule is subjected to physical stress, such as high temperature, multiple chromatography steps, ultracentrifugation, pumping, and stirring to name some examples. It also goes through chemical stress from exposure to salts, buffers, acids, and bases. This can lead to undesirable changes in the product, such as fragmentation, aggregation, or misfolding. The etanercept molecule is known to be sensitive to fragmentation (EP 1478394B1).

Formulation development is a considered to be a downstream unit operation which is focused on ensuring that the final product is conferred with a level of stability that will guarantee its safety and efficacy for the duration of its shelf-life. The development of an innovative or biosimilar mAb or Fc-fusion biopharmaceutical product for administration to human subjects requires a comprehensive characterization of its structural integrity, purity, and stability. The successful development of a robust formulation requires an understanding of the physical and chemical characteristics of the biopharmaceutical protein and the inactive ingredients alone and in combination. Inherent protein properties such as its tendency for self-association/aggregation, solubility and viscosity in solution pose challenges to the development of high concentration formulations. Achieving a suitable formulation requires an integrated approach whereby a stable formulation is developed that can be successfully administered and economically manufactured.

Each biopharmaceutical protein has unique characteristics that affects its solvent interaction, stability, hydrophobicity, and folding. The "structural differences among different proteins are so significant that generalization of universal stabilization strategies has not been successful" (Wang, W., *Intl. J. Pharm.* 185:129 (1999)). One of the most challenging tasks in the development of an aqueous or liquid formulation for a biopharmaceutical protein is dealing with its physical and chemical instabilities in a manner which preserves its biological activity for an acceptable shelf life. In practice the development of a formulation which confers stability to a particular biopharmaceutical protein requires balancing between destabilizing and stabilizing forces. This is particularly true with respect to recombinant fusion proteins, such as etanercept, which are characterized by a non-naturally occurring primary, secondary and tertiary structure.

Formulation development of a biopharmaceutical glycoprotein for therapeutic use presents distinct challenges not encountered during the formulation of synthetic small molecule agents. This is partially attributed to the considerations noted above regarding the inherent heterogeneity which characterizes the biological processes used to manufacture these types of therapeutic agents. It is also attributed to the fact that antibodies and Fc-containing fusion proteins are complex molecules characterized by a multi-domain three-dimensional structure composed of numerous reactive chemical groups. In addition, mAbs and Fc-fusion proteins are typically administered at relatively high doses (i.e., on the order of mg/kg), or via routes (i.e., subcutaneous), which requires that the use of a small (i.e., ≤1.5 ml) dose volume. In practice, typical concentration requirements for monoclonal antibodies and Fc-containing fusion proteins can range from 5 mg/ml to higher than 100 mg/ml. The development of high protein concentration formulations also facilitate the use of delivery options, such as prefilled syringes and autoinjector devices which are both amenable to chronic administration and which could improve patient compliance. These doses are significantly higher than those required for other classes of therapeutic proteins such as growth factors, clotting factors and cytokines or interleukins. Not surprisingly, the task of formulating a biological pharmaceutical at relatively high concentrations (e.g., >100 mg/ml) poses unique challenges.

It is well known that many aspects of biopharmaceutical production and formulation are pH sensitive. Maintaining the correct pH of a finished biopharmaceutical product is required to ensure the stability, effectiveness and shelf-life of the active agent. In order to maintain, pH pharmaceutical processes can use one or more buffering agents. A variety of buffering agents are available for pharmaceutical use. Selection of a suitable buffer requires a consideration of its buffering capacity, the solubility of the biopharmaceutical in the buffer and the desired pH of the formulation. The buffer should be stable and effective at maintaining pH over the range of conditions to which it will be exposed during formulation and storage of the product. It should not be deleteriously affected by oxidation or other reactions which could occur during the upstream or downstream unit operations required for the production and purification of the biopharmaceutical drug substance.

In practice, liquid formulation development results from a series of steps which require selection of an appropriate solution pH and of excipients selected to minimize degradation and promote stability of individual therapeutic agent. The choice of a formulation buffer species and molarity is one of the most significant aspects of the formulation development process. Selection of the buffer system and concentration is based on the buffer capacity required to stabilize the biopharmaceutical agent under the conditions to which the product will be exposed.

The pharmaceutical compositions of the invention comprise a buffer which functions, in part, to maintain the pH of the composition in a desired range. Numerous buffering agents are well know to those of skill in the art are known to be suitable for use in protein formulations are well known. Each of them works over a relatively narrow range of pH. Several factors need to be considered when choosing a buffer. For example, the buffer species and its concentration need to be defined based on its pKa and the desired formulation pH. Equally important is to ensure that the buffer is compatible with the protein drug, and any excipients that are present in the formulation. It is also important in pharmaceutical compositions to consider the possibility that a given buffering agent will be unacceptable for administration for ancillary reasons, such as deleterious effects on patient comfort. Some buffering agents are unsuitable for this purpose because they cause stinging or irritation at the point of administration. For example, citrate is known to cause stinging upon injection. Such effects are more pronounced for SC and IM administration, because the formulation remains at the administration site for some time, than for IV administration, where the formulation is diluted immediately.

Typical buffers used for biopharmaceuticals formulations include sodium or potassium phosphate, acetate, histidine, citrate and succinate. Citrate buffers (e.g., citrate-phosphate or citrate) are suitable for use in formulating etanercept. As disclosed herein, one buffer suitable for use in formulating etanercept is citrate-phosphate as its buffering capacity is at or near pH 2.2 to 7.8 or citrate which has a buffering capacity at or near pH 3.0 to 6.2. pH.

In various embodiments, an aqueous formulation can be prepared having a citrate or citate-phosphate buffer with a desired pH between about 6.0 and 6.6, sodium chloride, an amino acid selected from L-histidine and L-aspartic acid, a sugar selected from sucrose and trehalose and an effective amount of etanercept.

The phosphate component of the citrate-phosphate formulation can be supplied to the buffering system in a variety of different forms. For example, the phosphate component can be supplied as sodium phosphate, or potassium phosphate. It can be prepared with the acid form, monobasic form, dibasic form, or any combination thereof.

Citrate-phosphate buffer was prepared by first preparing a stock solution of citric acid and a stock solution of dibasic sodium phosphate. A citrate-phosphate stock solution was then prepared by titrating the citric acid stock solution into the dibasic sodium phosphate stock solution until the desired pH was attained. The citrate-phosphate stock solution was diluted to the final buffer concentration and the target pH was achieved by adding NaOH or HCl if necessary.

Citrate buffer was prepared by first preparing a stock solution of citric acid and a stock solution of sodium citrate. A citrate stock solution was then prepared by titrating the citric acid stock solution into the sodium citrate stock solution until the desired pH was attained. The citrate stock solution was diluted to the final buffer concentration and the target pH was achieved by adding NaOH or HCl if necessary.

In a particular embodiment, the invention provides a stabilized liquid formulation containing etanercept at 50 mg/ml, 1.5% (w/v) sucrose, 100 mM sodium chloride, 25 mM sodium phosphate, 25 mM L-lysine at pH 6.3.

In various embodiments, a citrate-phosphate buffer system having sufficient buffering capacity to maintain a target pH of about 6.0 to about 6.5 at a selected temperature can be use to prepare the formulations of the invention. Useful concentrations of sodium phosphate can be between about 5 to about 100 mM, between about 10 to about 75 mM, between about 10 to about 50 mM, between about 20 to about 30 mM. In various other embodiments, the sodium phosphate concentration can be about 10 mM, 15 mM, 20 mM, 25 mM, 30 mM, 35 mM, 40 mM, 45 mM, 50 mM Other concentrations of sodium phosphate can be appropriate provided that the buffer has sufficient buffering capacity to maintain the desired target pH, at a selected storage temperature.

In various embodiments, the citrate-phosphate buffered pharmaceutical formulation comprises sodium chloride concentration of more than about 75 mM. In alternative embodiments, the sodium chloride concentration can range from about 75 mM to about 125 mM. For example, the sodium chloride concentration can range from about 75 to about 100 mM. In particular embodiments, the sodium chloride concentration can be about 75 mM, about 80 mM, about 85 mM, about 90 mM, about 95 mM. about 100 mM, about 105 mM, about 110 mM or about 125 mM.

L-Histidine and L-Aspartic Acid were evaluated at 25 mM. The sucrose and/or trehalose concentration ranged from 1% to 8%. Specifically, sucrose 1% to 8% and trehalose from 1% to 2%.

In alternative embodiments, an aqueous formulation can be prepared having a citrate buffer with a desired pH, sodium chloride, and an effective amount of etanercept.

Selection of a target solution pH for the biopharmaceutical composition is a critical parameter that is often the first step performed during the development of a liquid biopharmaceutical formulation. Since individual biopharmaceutical proteins are characterized by different amino acid sequences and different isoelectric points (pI values), the optimal pH for a particular monoclonal antibody or fusion protein will differ based on the particular balance between various degradation processes. To ensure adequate solubility of a protein, the formulation pH should be at least 0.5 unit below or above its pI. The isoelectric point or pI of etanercept is 7.89. However, due to high levels of sialylation present on the molecule, the apparent pI of sialylated etanercept is in the range of 4.5 to 5.3.

In general, currently marketed biopharmaceuticals are formulated in the pH range of 5.0 to 7.2. When the pH of the pharmaceutical composition is set at or near physiological levels comfort of the patient upon administration is maximized. In particular, it is preferred that the pH be within a range of pH about 6.0 to 6.5. A suitable pH for etanercept-containing formulations should be below about 7.4 to prevent the solution from nearing the pI. A higher pH than the pI may lead to additional basicity induced degradation of the protein. In addition, the pH should not fall below about 5.3 to avoid the apparent pI of 4.80 of the sialylated molecule.

Generally speaking, formulation development involves optimizing the excipients present in a pharmaceutical composition (liquid or lyophilized powder) in order to minimize the physical (denaturation, aggregation) and/or chemical (oxidation, deamidation, isomerization, hydrolosis) degradation of the mAb or Fc-fusion protein. In drug formulation, the safety of the excipients present in a pharmaceutical composition is as important as the safety of the active product ingredient.

The structure of water surrounding a folded protein in an aqueous formulation is a critical for maintaining the structure of the protein and excipients are often added to stabilize this interaction Amino acids and sugars are commonly included in formulations in order to mediate a type of hydration effect. In the presence of a stabilizing excipient, a protein may preferentially hydrate which will have the effect of excluding the excipient, which will cause more water molecules to be found on the surface of the protein than in the bulk, which functions to stabilize the protein Jorgensen, L., *Expert Opin. Drug Deliv.* 6:11 (2009). Stabilization by this type of a hydration effect might be attributed to the prevention of the direct interaction between proteins which if left unchecked can promote protein aggregation. Arginine, has been previously reported to strongly bind to some proteins, and to be excluded from the surface of others Schneider, C. and Trout, B., *J. Phy. Chem. B.* 113:2050 (2009). The presence of arginine in the etanercept commercial formulation may stabilize etanercept against aggregation by suppressing protein-protein interactions ('702 patent).

Formulations in accordance with various aspects and embodiments of the invention may contain, among others, excipients which inhibit adsorption, prevent oxidation, maintain pH, stabilize the biopharmaceutical protein and control the osmolality of the pharmaceutical composition. In general, excipients can be chosen on the basis of the mechanisms by which they stabilize proteins against various chemical and physical stresses that could occur during a manufacturing process, under particular storage conditions, or associated with a particular mode of administration. In addition, an excipient can function as a diluent or employed to reduce the viscosity in high protein formulations in order to enable the delivery and/or enhance patient convenience.

The concentration or amount of an excipient to use in a formulation will vary depending on, for example, the amount of biopharmaceutical included in the formulation, the amount of other excipients included in the desired formulation, whether a diluent is needed, the amount or volume of other components in the formulation, and the desired tonicity or osmolality that is desired to be achieved. In various embodiments, different types of excipients can be combined in a single formulation. Accordingly, a single formulation can contain a singe excipient, two, three or more different types of excipients. Given the teachings and guidance provided herein, those skilled in the art can determine what amount or range of excipient can be included in a suitable formulation of the invention to achieve a formulation that promotes the retention of etanercept stability.

The use of excipients in liquid formulations is an established practice to stabilize proteins against degradation or aggregation processes attributed for instance, to stresses that occur during manufacturing, shipping, storage, pre-use preparation, or administration. In practice, the presence of a particular excipient in a formulation may have more than one effect or purpose.

A variety of publications and reviews are available on protein stabilization and formulation excipients useful in this regard, such as Arakawa, et al., "Solvent interactions in pharmaceutical formulations," *Pharm. Res.* 8(3):285-91 (1991); Kendrick, et al., "Physical stabilization of proteins in aqueous solution," in: *Rational Design of Stable Protein Formulations: Theory and Practice*, Carpenter and Manning, eds. *Pharmaceutical Biotechnology* 13:61-84 (2002), and Randolph, et al., "Surfactant-protein interactions," *Pharmaceutical Biotechnology* 13:159-75 (2002), each of which is herein incorporated by reference in its entirety, particularly in parts pertinent to excipients for formulations in accordance with the current invention, especially as to protein pharmaceutical products for veterinary and/or human medical uses.

The choice of excipients is often based on previous experience, this will be particularly true with regards to the formulation of biosimilar proteins, which will have to established to the satisfaction of regulatory authorities that a particular biosimilar formulation is "highly similar" to the reference product. For an excipient to be approved as part of a formulation approved for human use its inclusion has to be justified, the compatibility with the active ingredient established, and the quality (or grade) will have to shown to fulfill the requirements for the final product. The FDA has made a database and an "Inactive Ingredients Guide" from 1996 publicly available. The Inactive Ingredients Database provides information on inactive ingredients present in FDA-approved drug products. This information can be used by industry as an aid in developing drug products. For new drug development purposes, once an inactive ingredient has appeared in an approved drug product for a particular route of administration, the inactive ingredient is not considered new and may require a less extensive review the next time it is included in a new drug product. For example, if a particular inactive ingredient has been approved in a certain dosage form at a certain potency, a manufacturer could consider it safe for use in a similar manner for a similar type of product.

The optimum solubility of a biopharmaceutical protein is attributed to a combination of several parameters including, but not limited to, ionic strength, pH and solution composition, and a minimum solubility is often observed around the protein's pI value.

The osmolality of a pharmaceutical composition is preferably regulated in order to maximize the active ingredient's stability and also to minimize discomfort to the patient upon administration. A tonicity modifier is understood to be a molecule that contributes to the osmolality of a solution. Non-ionic and ionic agents may be used to adjust the osmolality (tonicity) of compositions in accordance with the invention, including many well known and other lesser known compounds useful for this purpose. Salts are useful in this regard, for instance. In embodiments, NaCl is used as a tonicifying agent. In embodiments KCl, LiCl or another salt is used as a tonicifying agent, alone or in combination with other tonicifying agents.

Salts may be used in accordance with embodiments of the invention to, for example, adjust the ionic strength and/or the isotonicity of a formulation and/or to improve the physical stability of a protein or other ingredient(s) of a composition. In embodiments salts prevent or reduce protein insolubility and/or aggregation. In embodiments salts also are effective for reducing the viscosity of protein formulations.

Polyols include sugars, e.g., mannitol, sucrose, trehalose and sorbitol and polyhydric alcohols such as, for instance, glycerol and propylene glycol. Generally, polyols are kosmotropic. Polyols are useful stabilizing agents in liquid and formulations to protect proteins from physical and chemical degradation processes, and can function to adjust the tonicity of formulations.

Tonicity agents and/or stabilizers included in a liquid formulation can be used, for example, to achieve a physiologic osmolality (e.g., isotonicity), of a formulation that is suitable for human or animal administration, or to facilitate the maintenance of a biopharmaceutical's structure, and/or to minimize electrostatic, solution protein-protein interactions. Examples of tonicity agents and/or stabilizers include polyols, salts and/or amino acids.

Aggregation inhibitors are added to pharmaceutical compositions to reduce a biopharmaceutical's tendency to associate in inappropriate or unwanted ternary or quaternary complexes.

Proteins in pharmaceutical compositions are susceptible to adsorption on surfaces and to denaturation and consequent aggregation at air-liquid, solid-liquid, and liquid-liquid interfaces. These effects generally scale inversely with protein concentration, and typically are exacerbated by physical agitation, such as that generated during the shipping and handling of a product. In practice, surfactants are commonly used to maintain protein conformational stability thereby minimizing, reducing or preventing surface adsorption. The use of surfactants in this regard is protein-specific, since any given surfactant typically will stabilize some proteins and destabilize others. Suitable surfactants for use in the invention in this regard include polysorbate 20, polysorbate 80, other fatty acid esters of sorbitan polyethoxylates, and poloxamer 188.

Filtration membranes are used throughout the purification process to remove impurities, to perform buffer exchange, and to concentrate the protein. In practice, ultrafiltration/diafiltration (UF/DF) is typically performed to exchange the buffer and to increase the protein concentration in solution. During the UF unit operation, the concentration of the biopharmaceutical protein at that membrane surface can be much higher than that of the bulk solution. Locally high concentrations can promote the formation of aggregates. In addition, the mechanical stresses that accompany multiple passes through the pump during the UF/DF process can also promote aggregation.

A pharmaceutical formulation comprising etanercept in one of the formulations of this invention is particularly useful for parenteral administration, i.e., subcutaneously, intramuscularly, intravenously, intraperitoneal, intracerebrospinal, intra-articular, intrasynovial, and/or intrathecal. Parenteral administration can be by bolus injection or continuous infusion. Pharmaceutical compositions for injection may be presented in unit dosage form, e.g., in ampoules or in multi-dose containers, with an added preservative.

A formulation of the invention can be administered, for example, with medical devices known in the art, such as pre-filled syringes and autoinjectors, such as, e.g., SureClick™, Inject-Ease™, Genject™, injector pens such as GenPen™, and needleless devices such as MediJector™ and BioJector™. The present pharmaceutical composition can also be adapted for yet to be discovered administration methods. The pharmaceutical compositions may, if desired, be presented in a vial, pack or dispenser device which may contain one or more unit dosage forms containing the active ingredient. In one embodiment the dispenser device can comprise a syringe having a single dose of the liquid formulation ready for injection. The syringe can be accompanied by instructions for administration.

Embodiments of the invention are not to be limited in scope by the specific embodiments described herein which are intended as illustrations of embodiments of the invention, and any compositions or methods which are functionally equivalent are within the scope of this invention. Various modifications of the invention in addition to those shown and described herein will become apparent to those skilled in the art form the foregoing description. Such modifications are intended to fall within the scope of the appended claims.

The specific embodiments described herein are offered by way of example only, and the invention is to be limited by the terms of the appended claims, along with the full scope of equivalents to which such claims are entitled.

EXAMPLES

Example 1

Production of TNFR:Fc in CHO Cells

Recombinant biosimilar etanercept comprising a soluble form of the human p75 TNF receptor fused to an Fc domain of a human immunoglobulin protein (TNFR:Fc) was expressed in Chinese Hamster Ovary cells. Post fermentation and harvest of the cells, the supernatant was subjected to a first round of purification using Protein A chromatography to capture the fusion protein, followed by virus inactivation at low pH. The process intermediate post virus inactivation was then neutralized and underwent two more rounds of purification, via mixed mode chromatography (ceramic hydroxyapatite resin), followed by hydrophobic interaction chromatography (HIC). Post HIC column purification, the process intermediate was subjected to virus filtration process via pressure filtration. The final process intermediate then underwent ultrafiltration/diafiltration into the final formulation buffer to achieve a final protein concentration between 27-33 mg/mL in 10 mM Tris, 1% sucrose, 4% mannitol pH ~7.5.

Alternatively, the fusion protein was buffer exchanged into 25 mM sodium phosphate, 1% sucrose, 100 mM sodium chloride, 25 mM Arginine pH 6.3 and concentrated to 50 mg/mL.

Example 2 pH Screen

Purpose:

The objective of the pH screen was to determine the optimal pH (range) based on stability and biophysical characterization.

Screen Design:

The pH screen was performed using an etanercept concentration of approximately 30 mg/mL. Formulations between pH 5.5-7.5 in 25 mM sodium phosphate buffer were placed on accelerated stability at 40° C. for up to 6 weeks. The samples were tested via pH, UV for protein concentration, OD 350 nm, HP-SEC and HIC.

The 25 mM sodium phosphate buffers were prepared by first preparing a 200 mM monobasic sodium phosphate stock solution and a 200 mM dibasic sodium phosphate stock solution. The stock solutions were then diluted to 25 mM. The 25 mM dibasic sodium phosphate solution was titrated into the 25 mM monobasic sodium phosphate solution until the desired pH was reached for each buffer.

Figure 2:
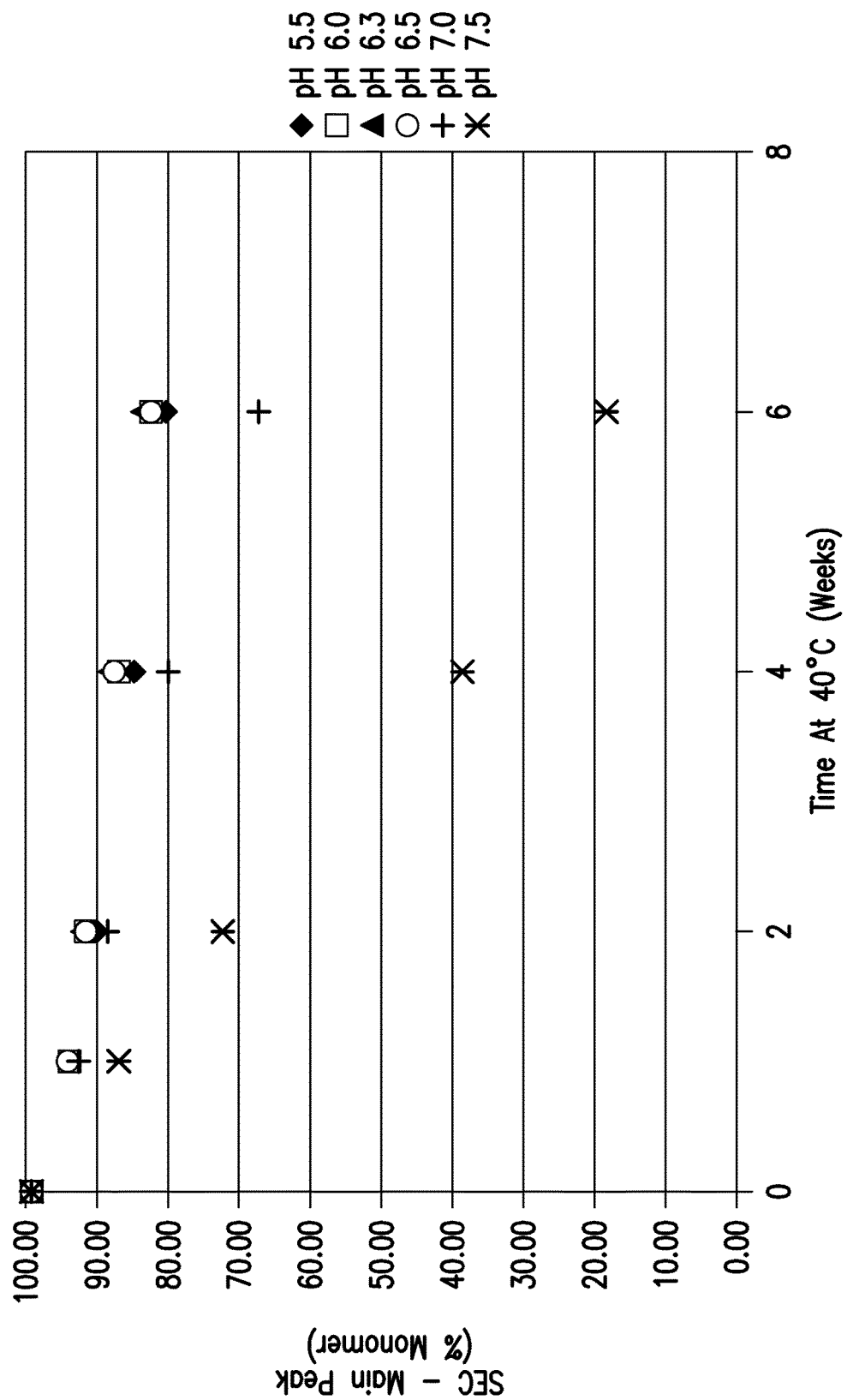
FIG. 2 provides a graphic representation of the results from a pH screening study summarizing the percentage monomer (SEC Main Peak) versus time (in weeks) for biosimilar etanercept under accelerated conditions (40° C.).
Figure 3:
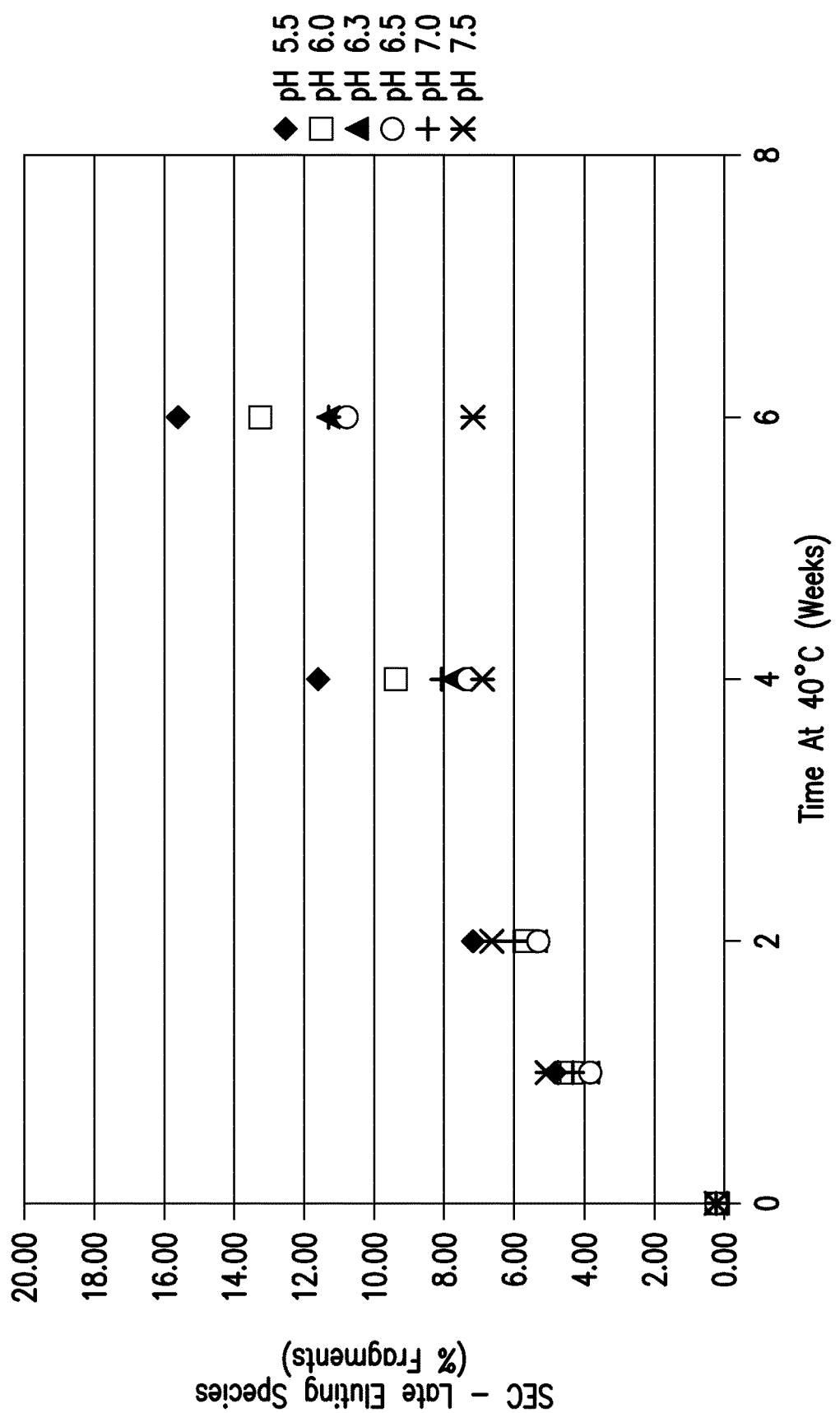
FIG. 3 provides a graphic representation of the results from a pH Screening Study summarizing the percentage of fragments (SEC Late eluting species) versus time (in weeks) for biosimilar etanercept under accelerated conditions (40° C.).

Data:

The HP-SEC data depicting % aggregates, % monomer and % fragments are shown in FIG. 1, FIG. 2, and FIG. 3, respectively. The formulations at pH 7.0 and 7.5 show a considerable increase in % aggregates over time, whereas the formulations at pH 5.5 and 6.0 show an increase in % fragments over time. The formulations with the highest % monomer are between pH 6.0-6.5.

Conclusion:

The biochemical stability data indicates the optimal pH for etanercept biosimilar is between pH 6.0-6.5.

Example 3

Buffer Screen

Purpose:

Having determined the optimal pH range for the etanercept biosimilar, a screen was performed to evaluate the stability of etanercept in potential buffers at pH 6.3.

Screen Design:

The buffer screen was performed using an etanercept concentration of approximately 30 mg/mL. Formulations comprised of the following buffers were placed on accelerated stability at 40° C. for up to 6 weeks: Citrate, Citrate Phosphate, Histidine, Maleate, Sodium Phosphate, Tris and Tris-Maleate. Citrate buffer was prepared by first preparing stock solutions of 25 mM citric acid and 25 mM sodium citrate. The citric acid solution was titrated into the sodium citrate solution until the desired pH was reached.

Citrate-phosphate buffer was prepared by first preparing stock solutions of citric acid and dibasic sodium phosphate heptahydrate. The citric acid solution was titrated into the sodium phosphate solution until the desired pH was reached. The resulting solution was diluted to the target concentration of 25 mM and the pH was adjusted with HCl.

Histidine buffer was prepared by first preparing stock solutions of 25 mM L-Histidine and 25 mM L-Histidine HCl Monohydrate. The L-Histidine HCl Monohydrate solution was titrated into the L-Histidine solution until the desired pH was reached.

Maleate buffer was prepared by making a 25 mM solution of maleic anhydride and adjusting to the desired pH with 1N NaOH.

Sodium Phosphate buffer was prepared by first preparing stock solutions of 25 mM monobasic sodium phosphate and 25 mM dibasic sodium phosphate. The monobasic sodium phosphate solution was titrated into the dibasic sodium phosphate solution until the desired pH was reached.

Tris buffer was prepared by making a 25 mM solution of Tris(hydroxymethyl)aminomethane and adjusting to the desired pH with 1N HCl.

Tris-Maleate buffer was prepared by combining the appropriate amounts of maleic anhydride and Tris(hydroxymethyl)aminomethane in water and adjusting to the desired pH with 1N NaOH.

The samples were tested via pH, UV for protein concentration, OD 350 nm, HP-SEC and HIC.

Figure 4:
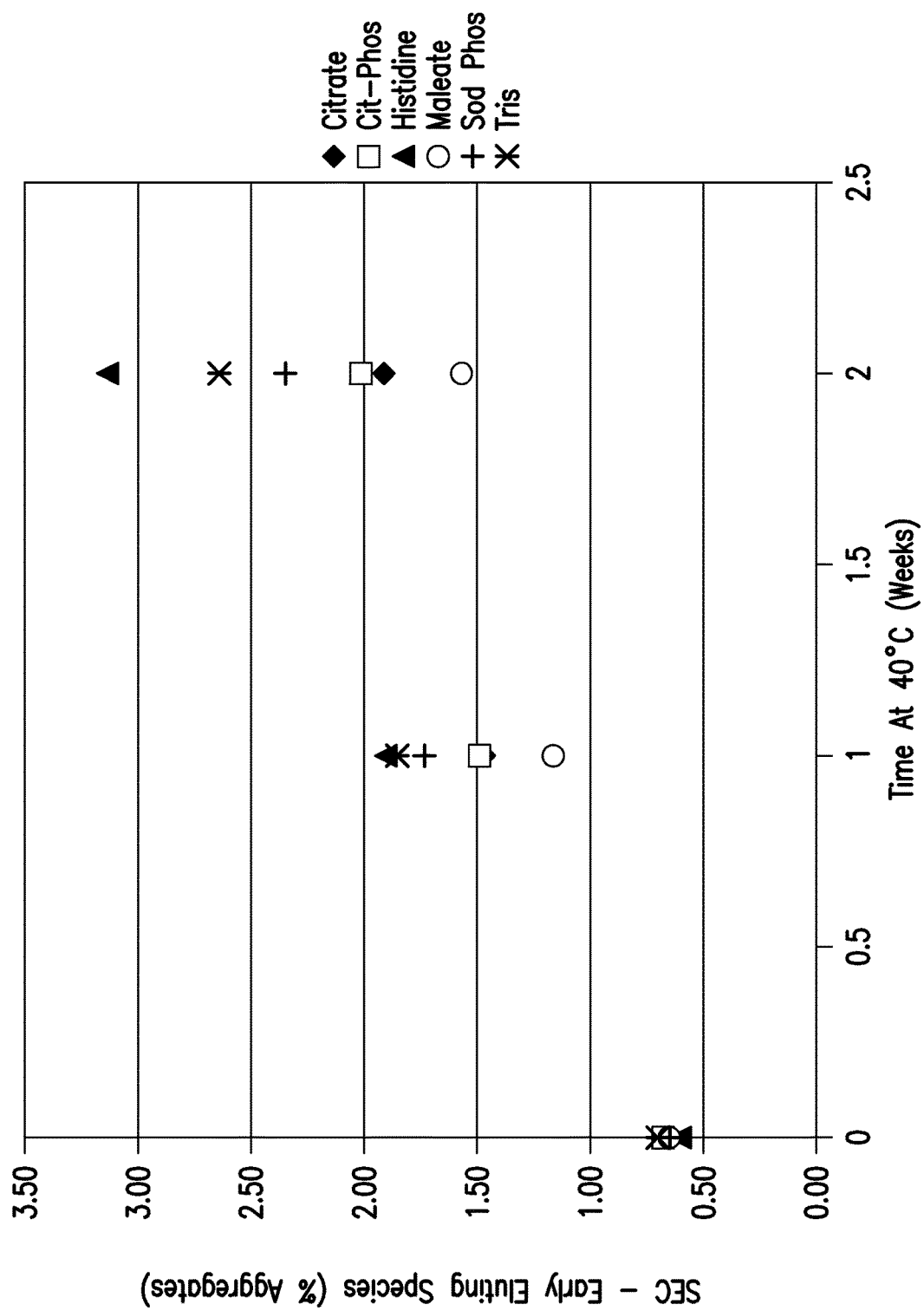
FIG. 4 provides a graphic representation of the results from a buffer screening study summarizing the percentage aggregates (SEC Early eluting species) versus time (in weeks) for etanercept biosimilar under accelerated conditions (40° C.).
Figure 5:
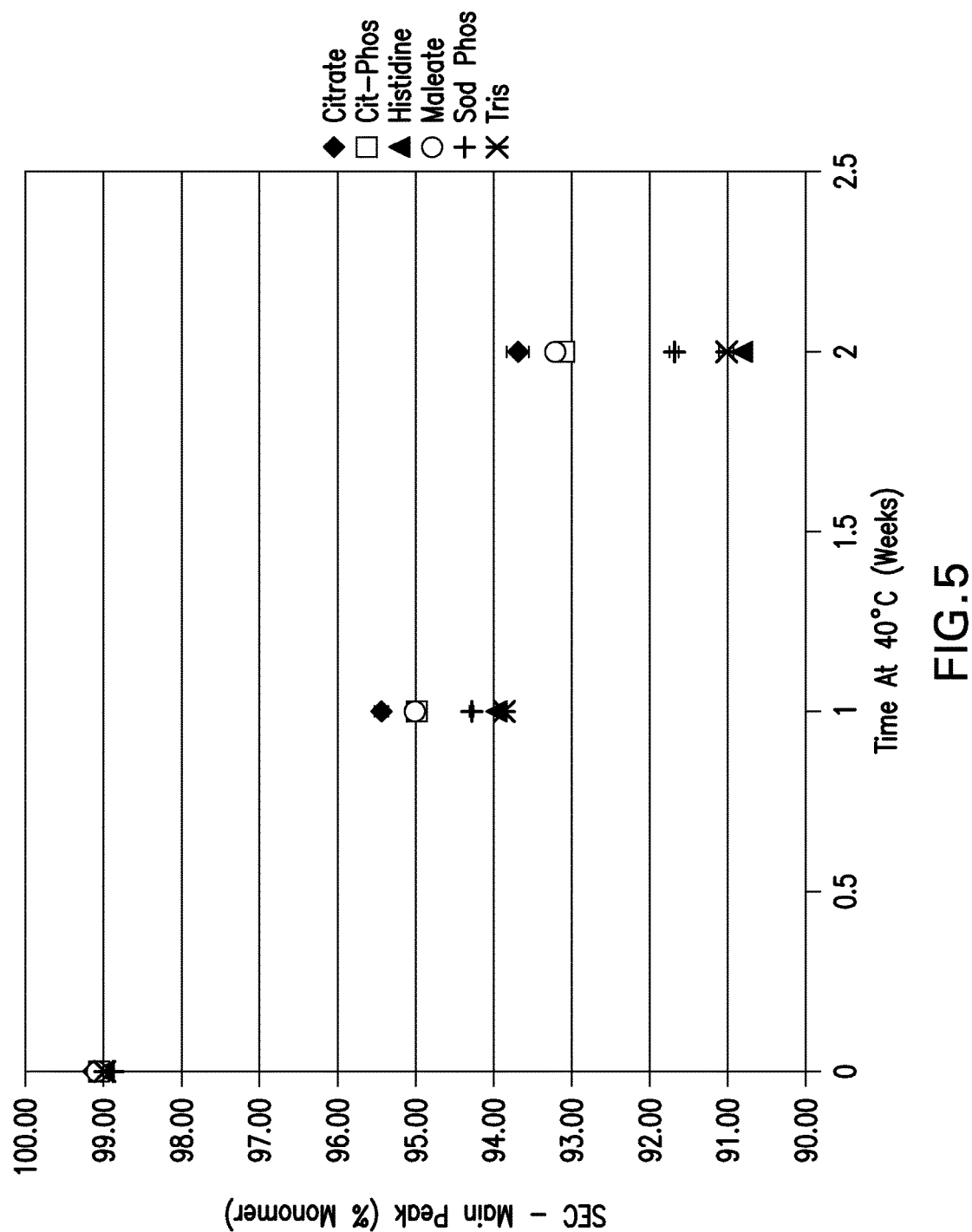
FIG. 5 provides a graphic representation of the results from a buffer screening study summarizing the percentage monomer (SEC Main Peak) versus time (in weeks) for biosimilar etanercept under accelerated conditions (40° C.).
Figure 6:
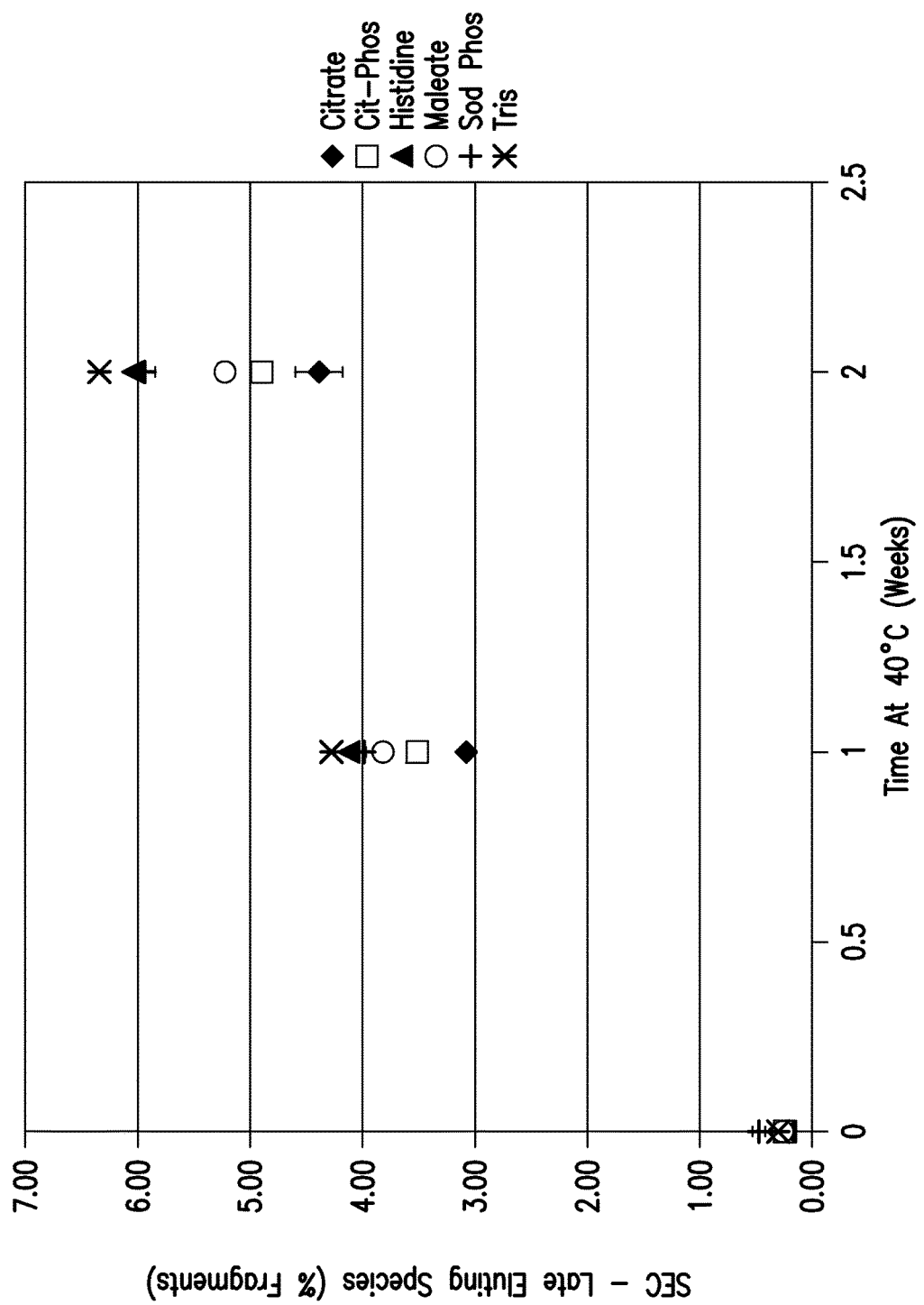
FIG. 6 provides a graphic representation of the results from a buffer screening study summarizing the percentage monomer (SEC Main Peak) versus time (in weeks) for biosimilar etanercept under accelerated conditions (40° C.).
Figure 7:
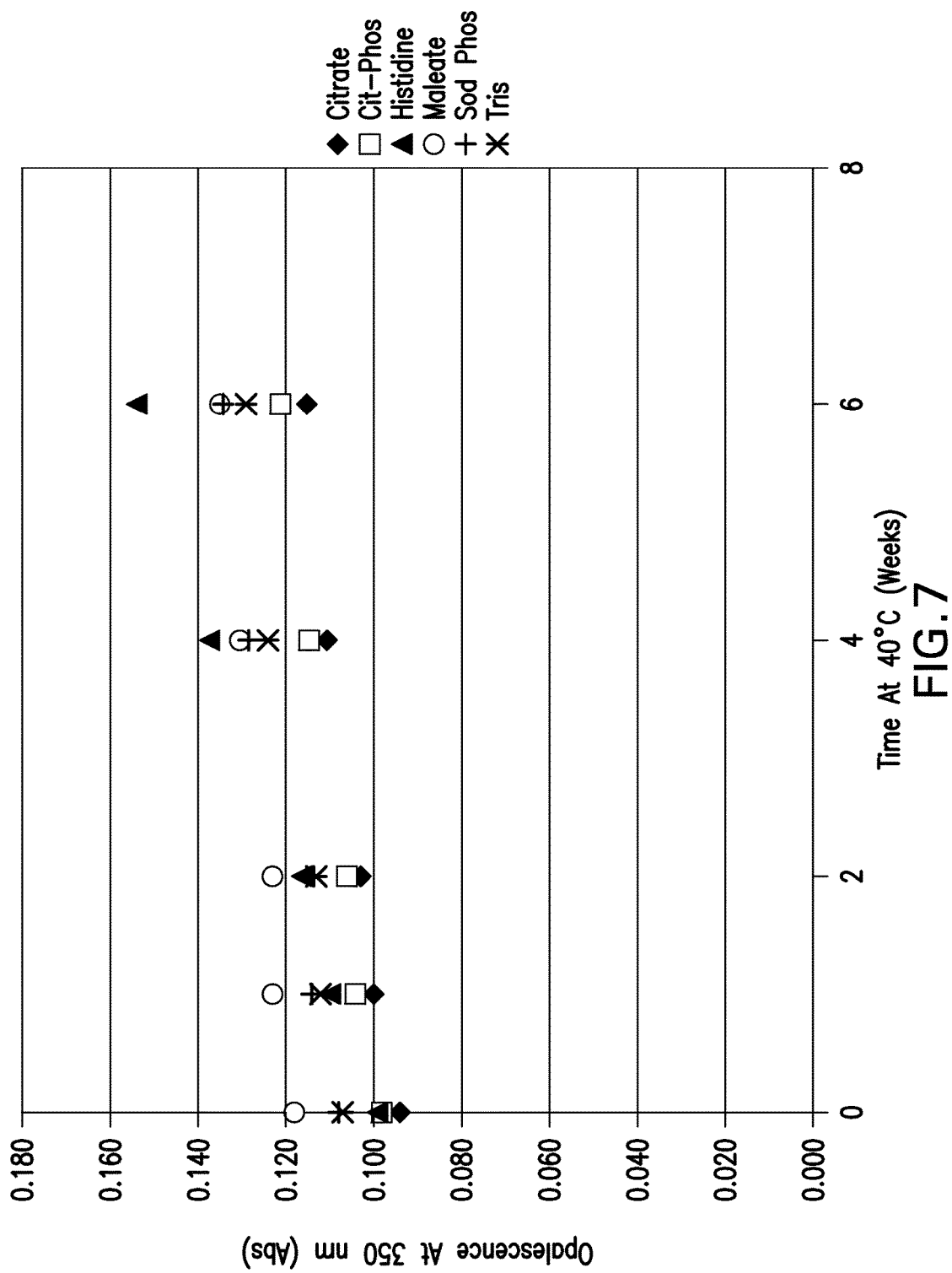
FIG. 7 provides a graphic representation of the results from a buffer screening study summarizing the opalescence at 350 nm for biosimilar etanercept under accelerated conditions (40° C.).

Data:

The HP-SEC data portraying % aggregate, % monomer and % fragments is shown in FIG. 4, FIG. 5, and FIG. 6, respectively. Maleate, Citrate and Citrate Phosphate buffers showed the lowest % aggregates and highest % monomer. The Citrate formulation had the lowest % fragments throughout the stability study. The OD 350 nm data depicting opalescence is plotted in FIG. 7. The citrate and citrate-phosphate formulations have the lowest opalescence throughout the stability study. (Note: Tris-Maleate data not shown due to rapid degradation of this formulation).

Conclusion:

The biochemical stability data indicated that the optimal buffers were Citrate, Citrate Phosphate and Maleate. Although the Maleate formulation showed low % aggregates on stability, a literature search revealed that no marketed therapeutic protein formulation used maleate as a buffer system. Therefore, only Citrate and Citrate Phosphate were selected as the buffers to move forward in the next round of formulation development studies.

Example 4

Excipient Screen

Purpose:

Understand the role of each excipient in the originator formulation and screen potential sugar, salt and amino acid stabilizers.

Screen Design:

The excipient screen was performed using an etanercept concentration of approximately 50 mg/mL. The formulations were all in 25 mM sodium phosphate buffer. 25 mM sodium phosphate buffer was prepared by first making stock solutions of monobasic sodium phosphate and dibasic sodium phosphate. The monobasic sodium phosphate solution was titrated into the dibasic sodium phosphate solution until the desired pH of 6.3 was reached. The resulting sodium phosphate solution was diluted to 25 mM. The protein was dialyzed into 25 mM sodium phosphate buffer and concentrated to approximately 69 mg/mL.

High concentration stock solutions of excipients and amino acids were prepared in 25 mM sodium phosphate buffer and pH adjusted to 6.3 using NaOH or HCl as needed. The excipient stock solutions were spiked into the protein solution at the appropriate ratios to achieve the desired final concentrations of protein and excipients.

Formulations in 25 mM sodium phosphate buffer at pH 6.3 with various concentrations of sugars, sodium chloride and amino acids were placed on accelerated stability at 40° C. for up to 8 weeks. A summary table of all the formulations is provided below (see Table 2). The samples were tested by pH, UV for protein concentration, OD 350 nm, HP-SEC, HIC and DSC.

TABLE 2

Summary of formulations evaluated in the excipient screen

| Code | Formulation |
| --- | --- |
| A1 | Hanwha Drug Substance in 25 mM sodium phosphate buffer, 25 mM L-Arg HCl, 100 mM NaCl, 1% sucrose |
| A2 | 25 mM sodium phosphate buffer, 25 mM L-Arg HCl, 100 mM NaCl, 1% sucrose |
| A3 | 25 mM sodium phosphate buffer, pH 6.3 |
| A4 | 25 mM sodium phosphate buffer, 25 mM L-Arg HCl |
| A5 | 25 mM sodium phosphate buffer, 100 mM NaCl |
| A6 | 25 mM sodium phosphate buffer, 8% sucrose |
| A7 | 25 mM sodium phosphate buffer, 100 mM NaCl, 1% sucrose |
| A8 | 25 mM sodium phosphate buffer, 25 mM L-Arg HCl, 6% sucrose |
| A9 | 25 mM sodium phosphate buffer, 5% sorbitol |
| A10 | 25 mM sodium phosphate buffer, 25 mM L-Arg HCl, 3.6% sorbitol |
| A11 | 25 mM sodium phosphate buffer, 25 mM L-His HCl, 100 mM NaCl, 1% sucrose |
| A12 | 25 mM sodium phosphate buffer, 25 mM L-Lys, 100 mM NaCl, 1% sucrose |
| A13 | 25 mM sodium phosphate buffer, 25 mM L-Asp, 100 mM NaCl, 1% sucrose |
| A14 | 25 mM sodium phosphate buffer, 25 mM L-Pro, 100 mM NaCl, 1% sucrose |
| A15 | 25 mM sodium phosphate buffer, 25 mM L-Cys HCl, 100 mM NaCl, 1% sucrose |
| A16 | 25 mM sodium phosphate buffer, 25 mM Gly, 100 mM NaCl, 1% sucrose |

Figure 8:
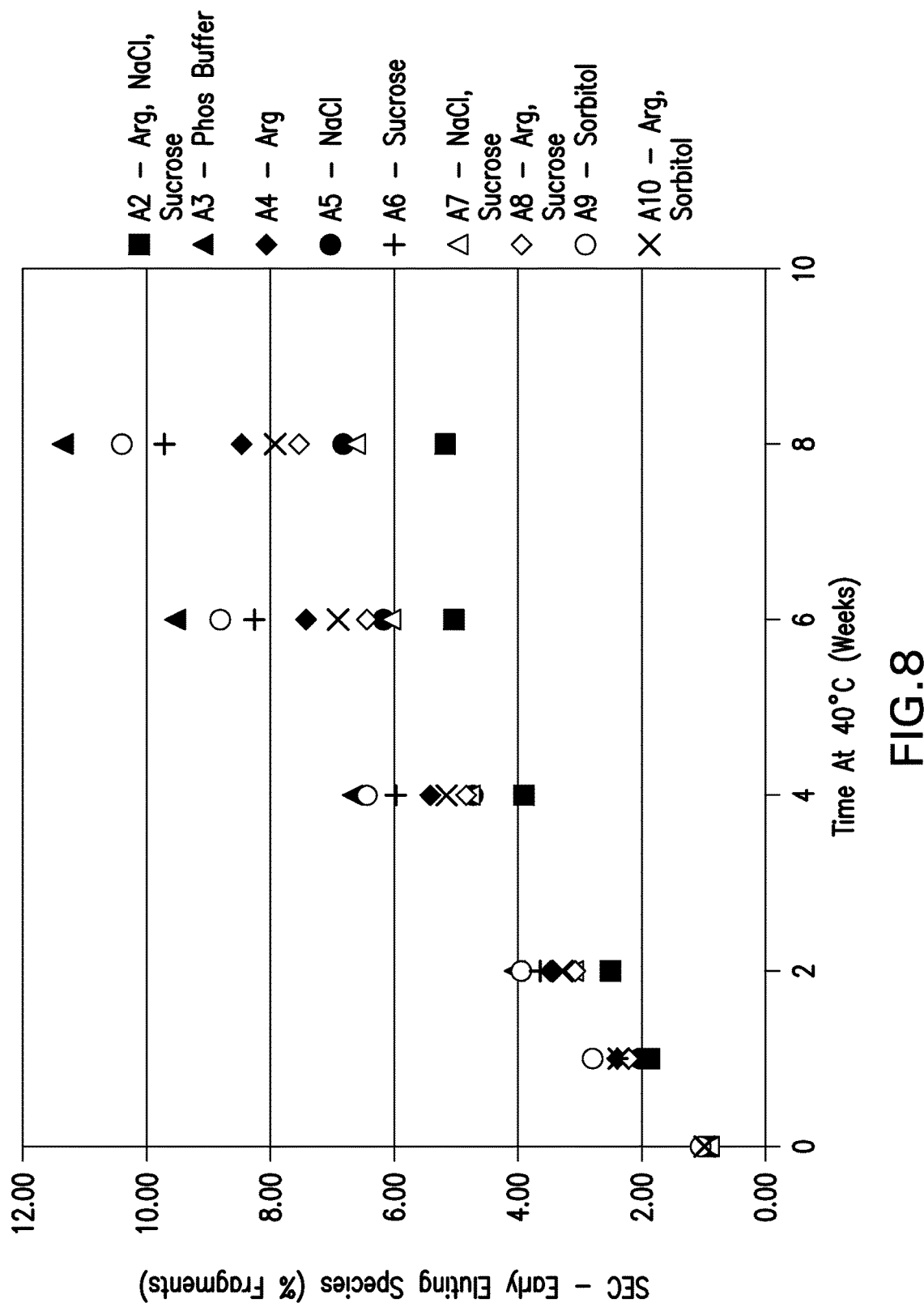
FIG. 8 provides a graphic representation of the results from an excipient screening study summarizing the effect of various sugar/salt stabilizer combinations on the percentage aggregates (SEC Early eluting species) for biosimilar etanercept under accelerated conditions (40° C.).
Figure 9:
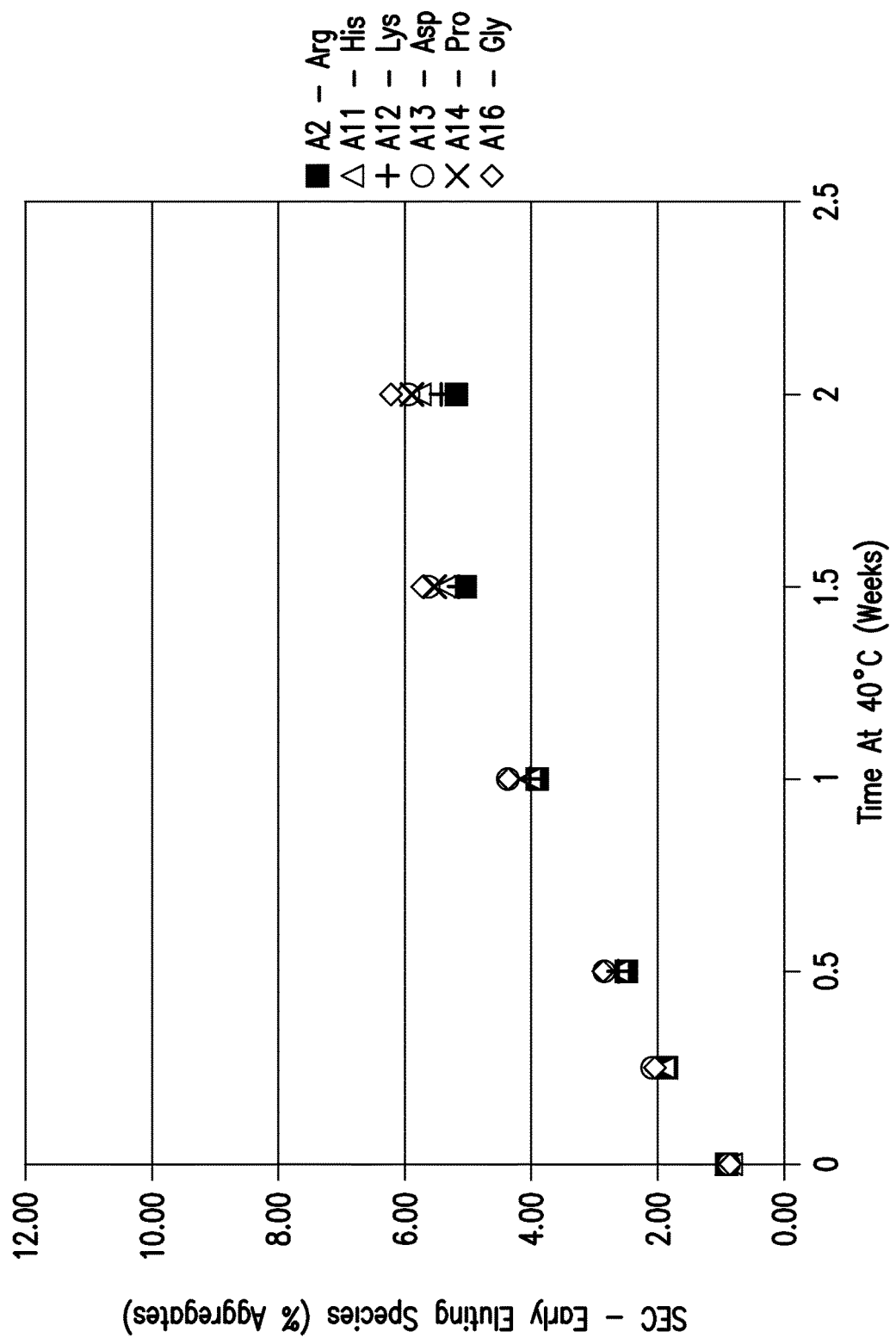
FIG. 9 provides a graphic representation of the results from an excipient screening study summarizing the effect of various amino acid stabilizers on the percentage of aggregates (SEC Early eluting species) for biosimilar etanercept under accelerated conditions (40° C.).

Data:

The HP-SEC data depicting % aggregates for the excipient screen is shown in FIG. 8 and FIG. 9. As seen in FIG. 8, formulations with sodium chloride exhibit lower % aggregates compared to formulations without sodium chloride. Sugars such as such as sucrose and sorbitol contribute to stability, though not as significantly as sodium chloride. Formulations with sucrose show marginally better stability compared to sorbitol. FIG. 9 portrays that while the innovator formulation containing Arginine has the lowest % aggregates, other amino acids such as Histidine, Lysine, Aspartic Acid, Proline and Glycine could also act as stabilizers and potentially replace Arginine.

Overall Conclusion:

Based on biochemical stability data and biophysical characterization, sodium chloride was deemed important for stability at an etanercept concentration between 25 to 50 mg/mL. The data also showed that incorporating sugars could improve stability but could not be a replacement for sodium chloride. Several amino acids could potentially replace arginine as a stabilizer. In the next round of screening studies, different concentrations of sodium chloride were evaluated. In addition, the impact of including Histidine, Aspartic Acid, Sucrose and Trehalose as potential stabilizers was investigated.

Example 5

DOE Study

Purpose:

Understand the impact of pH, buffer, sodium chloride, amino acid type and sugar type on improving the stability of etanercept biosimilar. Determine if there are interaction effects between each factor and establish a design space for formulation parameters.

Figure 10:
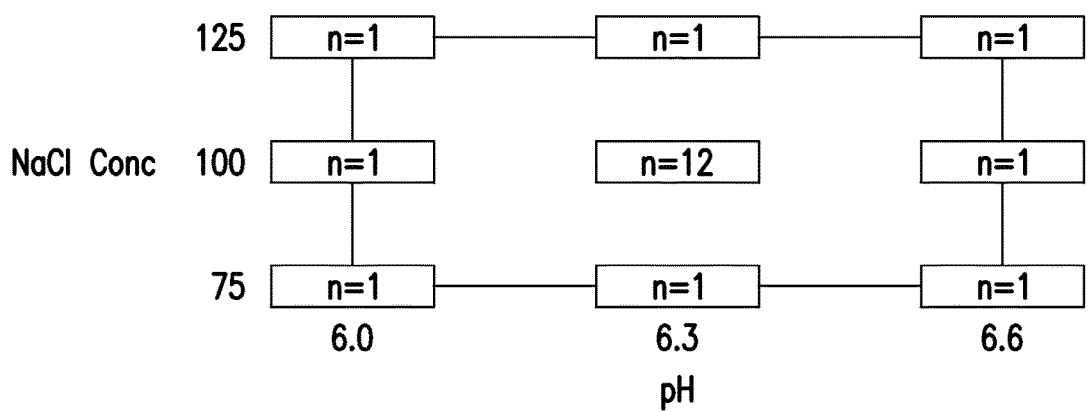
FIG. 10 provides a graphic representation of the DOE study design performed to investigate the impact of buffer type, sugar type, amino acid type, pH and NaCl concentration on stability of biosimilar etanercept.

Study Design:

The DOE study was designed to study both categorical factors (buffer type, sugar type and amino acid type) and continuous factors (pH value, NaCl/Sugar concentration) simultaneously. FIG. 10 is a pictorial view of the study design.

At the center point, the following factors were held constant
  pH: 6.
  NaCl concentration: 100 mM
  Sugar concentration: 1%
  The effect of the following categorical factors were evaluated:
  Buffer (sodium phosphate, citrate phosphate, or citrate)
  Sugar: Trehalose, Sucrose
  Amino Acid: L-His, L-Asp
  Along the perimeter of the study design, the following factors were held constant:
  Buffer type: citrate phosphate
  Sugar type: Trehalose
  Amino Acid type: 25 mM L-His
  The following continuous factors were studied:
  pH: 6.0, 6.3, 6.6
  NaCl/Sugar concentration: 75 mM NaCl/2% sugar, 100 mM NaCl/1% sugar, 125 mM NaCl/0% sugar The DOE was performed using an etanercept concentration of approximately 50 mg/mL. The protein was dialyzed into either 25 mM sodium phosphate buffer pH 6.3, 25 mM citrate-phosphate buffer pH 6.3, 25 mM citrate-phosphate buffer pH 6.0, 25 mM citrate-phosphate buffer pH 6.6 or 10 mM citrate buffer pH 6.3.

Citrate buffer was prepared by first preparing stock solutions of 10 mM citric acid and 10 mM sodium citrate. The citric acid solution was titrated into the sodium citrate solution until the desired pH was reached.

Citrate-phosphate buffer was prepared by first preparing stock solutions of citric acid and dibasic sodium phosphate heptahydrate. The citric acid solution was titrated into the sodium phosphate solution until the desired pH was reached. The resulting solution was diluted to the target concentration of 25 mM and the pH was adjusted with HCl.

Sodium Phosphate buffer was prepared by first preparing stock solutions of 25 mM monobasic sodium phosphate and 25 mM dibasic sodium phosphate. The monobasic sodium phosphate solution was titrated into the dibasic sodium phosphate solution until the desired pH was reached.

After protein dialysis, each protein solution was concentrated to 70-80 mg/mL. High concentration stock solutions of excipients were prepared in the appropriate formulation buffer and pH adjusted using NaOH or HCl as needed. The excipient stock solutions were spiked into the protein solutions at the appropriate ratios to achieve the desired final concentrations of protein and excipients.

Figure 11:
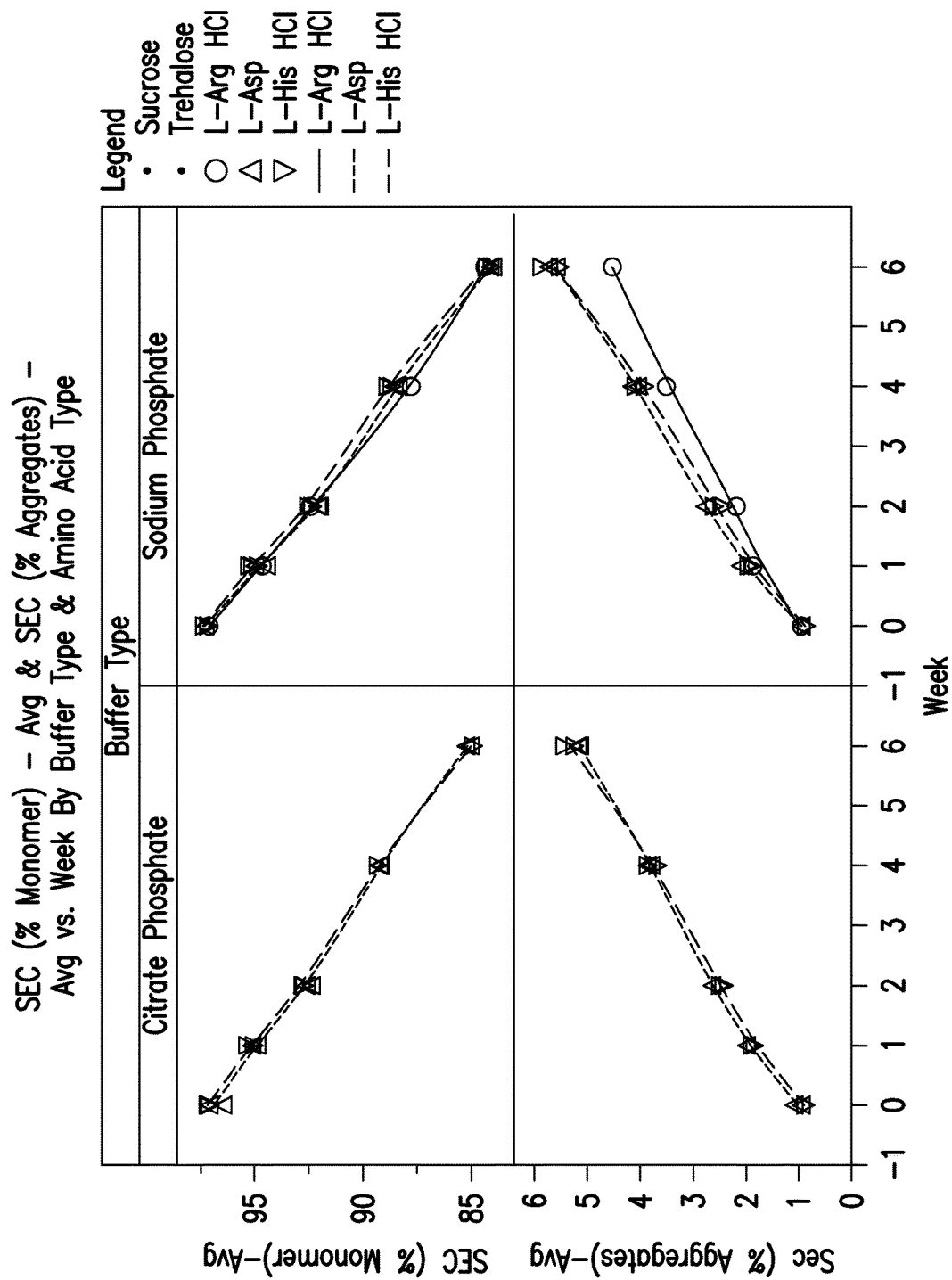
FIG. 11 provides a graphic representation of the effect of buffer type, sugar type and amino acid type on % aggregates and % monomer using SEC analysis as a function of time on stability at 40° C.
Figure 12:
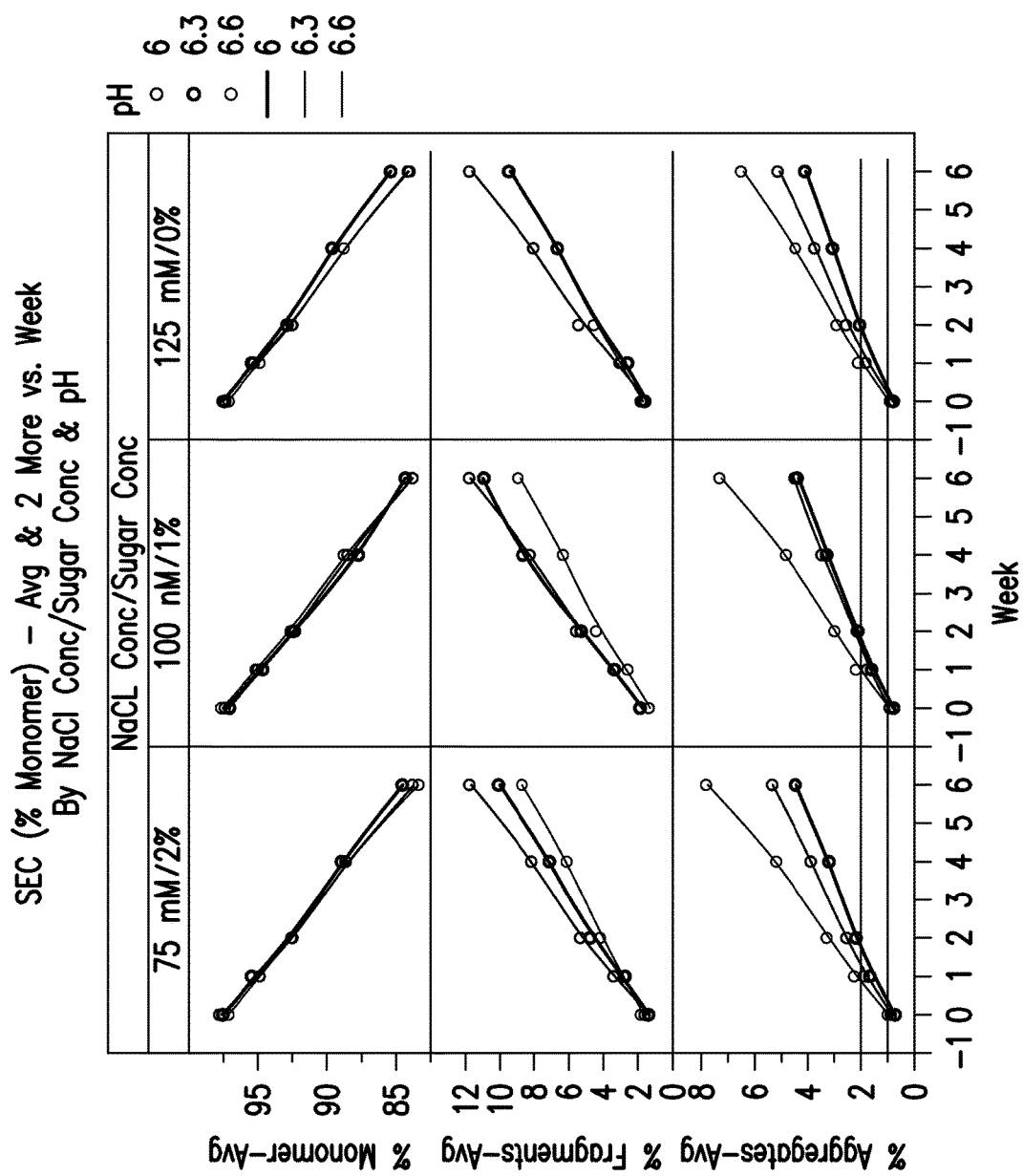
FIG. 12 provides a graphic representation of the effect of pH and sodium chloride concentration on % aggregates, % fragments and % monomer using SEC analysis as a function of time on stability at 40° C.

Data:

FIG. 11 shows the effect of buffer type (citrate phosphate, sodium phosphate), amino acid type (L-His, L-Arg, L-Asp) and sugar type (sucrose, trehalose) on % aggregates and % monomer as a function of time on stability using HP-SEC. L-Arg HCl in the innovator formulation is associated with lower % aggregates and is less impacted by time on stability. There is no significant difference between L-His HCl and L-Asp in term of lower % aggregates and higher % monomer. Citrate phosphate buffer was linked to lower % aggregates and higher % monomer compared to sodium phosphate buffer. The effect of sugar type does not seem to be important and there is no significant difference between sucrose and trehalose. FIG. 12 shows the effect of pH and NaCl/sugar concentrations on % aggregates, % fragments and % monomer. The pH is a significant factor for % aggregates and % fragments, but not for % monomer. Lower pH is associated with a slower rate of increase in % aggregates over time, but the opposite effect is observed for % fragments. This is observed independently of the NaCl concentration. Increasing NaCl concentration is associated with lower values of % aggregates when pH is in the upper range but seems to have no effect in the lower pH range.

Conclusion:

The criterion for deciding the lead formulations was based on selecting formulation components that minimized % aggregates. Based on the DOE study, the following conclusions were made:
  Amino Acid type: No significant difference between L-Asp and L-His. L-Arg in the innovator formulation showed slower rate of increase in % aggregates.
  Buffer type: Citrate phosphate and citrate associated with slower rate of % aggregates compared to sodium phosphate.
  Sugar type: No significant difference between sucrose and trehalose
  pH: Lower pH associated with slower rate of % aggregates. However, lower pH was also associated with faster rate of % fragments.
  NaCl concentration: Higher NaCl concentration associated with lower % aggregates when pH is high, but no significant impact at low pH.

Based on the conclusions of the DOE study, formulations with the following components were placed on stability at an etanercept concentration of 50 mg/mL: pH 6.0 or 6.3, citrate phosphate or citrate buffer, 100 mM or 125 mM NaCl, L-His or L-Asp, sucrose or trehalose.

Example 6

Preliminary PK-Study

Purpose:
To compare the PK of etanercept biosimilar in three novel citrate based formulations versus the originator liquid formulation.

Study Design:
Etanercept biosimilar drug substance was reformulated into three novel citrate based liquid formulations and originator liquid formulation. The concentration of all etanercept formulations was 50 mg/mL. Male Sprague Dawley rats were dosed at 1 mg/kg via subcutaneous administration (N=6). Timepoints were taken initially and every 24 hours for 8 days. Key pharmokinetic parameters determined from the rat PK study are set forth in Table 3.

Formulation 1: 25 mM Citrate-Phosphate, 100 mM NaCl, 25 mM His, 1% Sucrose, pH 6.3
Formulation 2: 25 mM Citrate-Phosphate, 125 mM NaCl, 25 mM His, 1% Trehalose, pH 6.0
Formulation 3: 10 mM Citrate, 100 mM-NaCl, 25 mM Aspartic acid, 1% Trehalose, pH 6.3
Enbrel Formulation: 25 mM Na-Phosphate, 100 mM NaCl, 25 mM Arginine, 1% Sucrose, pH 6.3.

Figure 13:
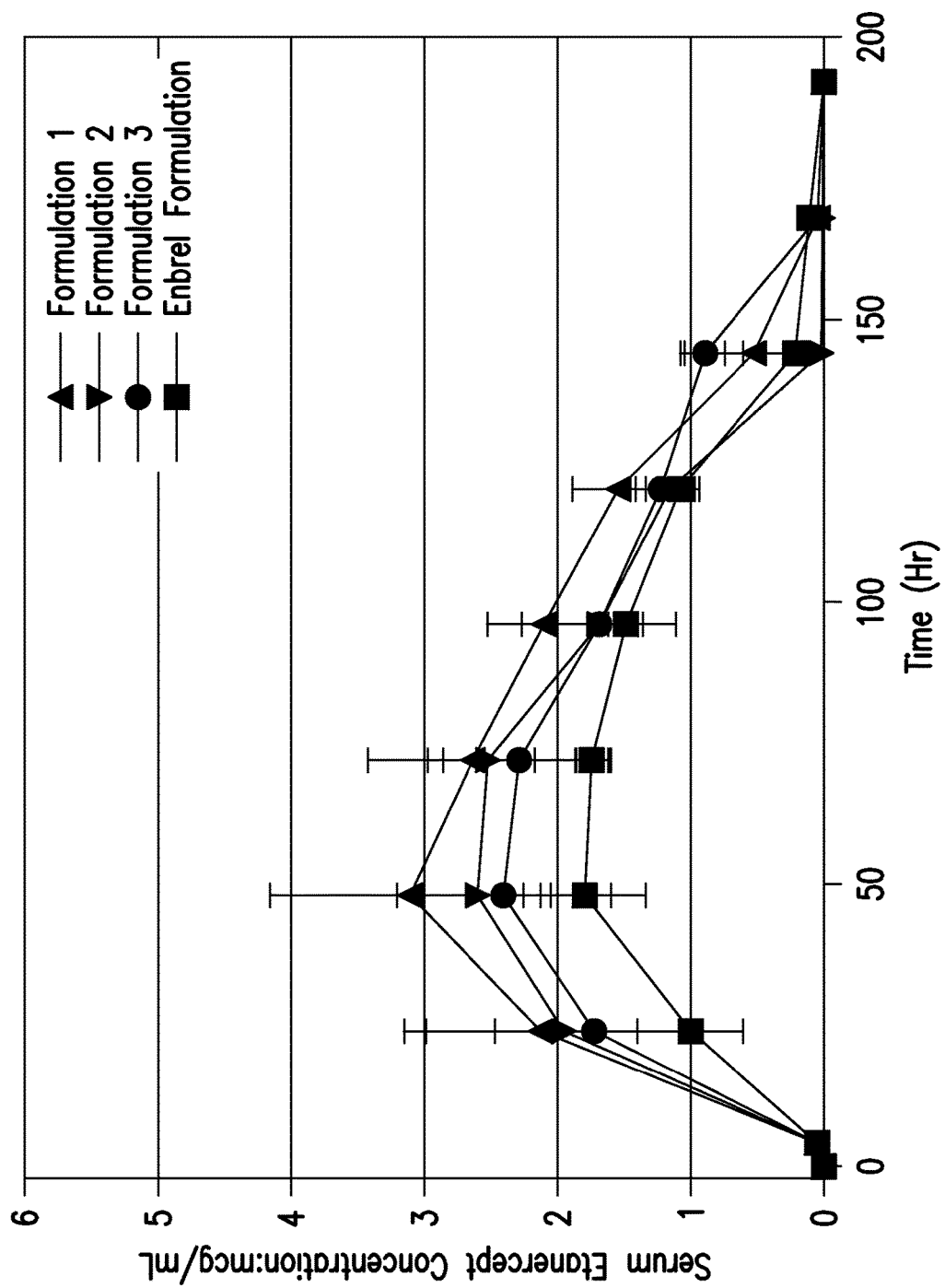
FIG. 13 provides a graphic representation of serum concentration of biosimilar etanercept versus time (hours) observed in rats after subcutaneous administration during a preliminary pharmacokinetic (PK) study evaluating different formulations.

Data:
Results from the PK study are presented in FIG. 13 and in Table 3.

TABLE 3

|  | FORMULATION 1 | FORMULATION 2 | FORMULATION 3 | ENBREL FORMULATION |
|---|---|---|---|---|
| $C_{MAX}$ (MG/ML) | 3.10 ± 1.05 | 2.76 ± 0.57 | 2.65 ± 0.80 | 1.91 ± 0.0.37 |
| $T_{MAX}$ (HR) | 48 ± 0 | 52 ± 18 | 60 ± 13 | 68 ± 18 |
| $AUC_{LAST}$ (HR * MG/ML) | 283 ± 88 | 235 ± 56 | 241 ± 49 | 173 ± 24 |
| $AUC_{0-IFN}$ ((HR * MG/ML) | 302 ± 96 | 235 ± 56 | 316 ± 56 | 174 ± 23 |

Conclusion:
Based on the PK data, there is no significant difference in the pharmacokinetics between etanercept biosimilar in the citrate based formulations, or in the originator (Enbrel) formulation. They show overall similar exposure.

Example 7

Stability Study

Purpose:
Select final formulation by placing three lead formulations on long-term stability at 50 mg/mL for up to 6 months.

Study Design:
Place the biosimilar etanercept polypeptide in the three lead formulations and the Enbrel reference product (Innovator protein in commercial formulation) on long-term stability for up to 6 months at 5, 25 and 40° C. (Table).

The formulations were filled in both vials and pre-filled syringes. The samples will be tested using the following analytical methods: ELISA, Cell-based assay, UV, cIEF, reducing and non-reducing CD-SDS, HI-HPLC, SE-HPLC, CEX, Peptide Mapping, MFI, A350, Osmolality, pH, Appearance, DSC, DLS, Far-CD, AUC, and ANS binding.

TABLE 4

| Product | pH | Buffer (mM) | NaCl (mM) | Amino Acid (mM) | Sugar |
|---|---|---|---|---|---|
| Enbrel ® | 6.3 ± 0.2 | 25 Sodium phosphate | 100 | 25 Arg | 1% Sucrose |
| Biosimilar Formulation #1 | 6.3 | 25 Citrate-Phosphate | 100 | 25 His | 1% Sucrose |
| Biosimilar Formulation #2 | 6.0 | 25 Citrate-Phosphate | 125 | 25 His | 1% Trehalose |
| Biosimilar Formulation #3 | 6.3 | 10 Citrate | 100 | 25 Asp | 1% Trehalose |

All of the above demonstrates that stability of biosimilar etanercept as analyzed by aggregation, misfolding, fragmentation and binding, is comparable or improved when compared to the arginine containing formulation used in the reference product. As such, formulations containing sodium chloride, L-histidine or L-aspartic acid, sucrose or trehalose, buffered by citrate-phosphate or citrate to a pH between about 6.0 or 6.3 provide novel alternative liquid formulations for long-term storage of etanercept-containing solutions.

Other embodiments are within the following claims. While several embodiments have been shown and described, various modifications may be made without departing from the spirit and scope of the present invention.

REFERENCES

Arakawa, T., Tsumoto, K., Kita, Y., Chang, B., Ejima, D., "Biotechnology applications of amino acids in protein purification and formulations", *Amino Acids* 2007 33 pp. 587-605

Dore, R K, Mathews, S., Schechtman, Jr., Surbeck, W., Mandel D., Patel, A., Zhou, L., Peloso, P., "The immunogenicity, safety, and efficacy of etanercept liquid administered once weekly in patients with rheumatoid arthritis", *Clin. Exp. Rheumatol.* 2007 25(1) pp. 40-46

Goffe and Cather, "Etanercept: An overview" *J. Am. Acad. Dermatol.*, 2003 49 pp. 105-111

Schiestl M, Stangler T, Torella C, Cepeljnik T, Toll H, Grau R., "Acceptable changes in quality attributes of glycosylated biopharmaceuticals", *Nature Biotechnology* 2011 29(4) pp. 310-312

Sullivan, J., et al., "Bioequivalence of Liquid and Reconstituted Lyophilized Etanercept Subcutaneous Injections", *Journal of Clinical Pharmacology,* 2006 46 pp. 654-661

Van Maarschalkerweerd A, Wolbink G, Stapel S, Jiskoot W, Hawe A., "Comparison of analytical methods to detect instability of etanercept during thermal stress testing", *European Journal of Pharmaceutics and Biopharmaceutics*, 2011 78 pp. 213-221

Wang, W., "Instability, stabilization, and formulation of liquid protein pharmaceuticals", *Int. J Pharmaceutics* 1999 185(2) pp. 129-188, Wang, W., Singh, S., Zeng, D. L., King, K., Nema, S., "Antibody structure, instability, and formulation", *J. of Pharmaceutical Sciences* 2007 96(1) pp. 1-26

Yi, SoJeong, Kim, Sung Eun, Park, Min-Kyu, Yoon, Seo Hyun, Cho, Joo-Youn, Lim, Kyioung Soo, Shin, Sang-Goo, Jang, In-Jin, Yu, Kyung-Sang, "Comparative pharmacokinetics of HD203, a biosimilar of etanercept, with marketed etanercept (Enbrel®)", *Biodrugs* 2012 26(3) pp. 177-184

Zhou, H., Buckwalter, M., Boni, J., Mayer, P., Raible, D., Wajdula, J., Fatenejad, S., Sanda, M., "Population-based pharmacokinetics of the soluble TNFr etanercept: a clinical study in 43 patients with ankylosing spondylitis compared with post hoc data from patients with rheumatoid arthritis", *Int. J. Clin. Pharm. Ther.,* 2004 42(5) pp. 267-276

What is claimed:

1. A stable liquid pharmaceutical formulation comprising 50 mg/ml etanercept, a citrate-phosphate buffer, 100 or 125 mM sodium chloride, L-histidine, and sucrose, pH 6.0-6.5.

2. The formulation of claim 1, wherein the amino acid is L-histidine at a concentration of 25 mM.

3. The formulation of claim 2, wherein the sugar is present at a concentration of about 1%.

4. The formulation of claim 1, comprising 50 mg/ml etanercept, a 25 mM citrate-phosphate buffer pH 6.3, 100 mM sodium chloride, 25 mM L-histidine and 1% sucrose.

5. The formulation of claim 1 wherein etanercept exhibits stability over at least about 12 months.

* * * * *